United States Patent
Just et al.

(10) Patent No.: US 11,266,319 B2
(45) Date of Patent: Mar. 8, 2022

(54) PHYSIOLOGICAL MONITORING DEVICES HAVING SENSING ELEMENTS DECOUPLED FROM BODY MOTION

(71) Applicant: Valencell, Inc., Raleigh, NC (US)

(72) Inventors: Steven Matthew Just, Cary, NC (US); Jesse Berkley Tucker, Youngsville, NC (US); Robert Splinter, Durham, NC (US); Steven Francis LeBoeuf, Raleigh, NC (US)

(73) Assignee: Valencell, Inc., Raleigh, NC (US)

( * ) Notice: Subject to any disclaimer, the term of this patent is extended or adjusted under 35 U.S.C. 154(b) by 230 days.

(21) Appl. No.: 16/238,921

(22) Filed: Jan. 3, 2019

(65) Prior Publication Data
US 2019/0133469 A1    May 9, 2019

Related U.S. Application Data

(63) Continuation of application No. 14/761,462, filed as application No. PCT/US2014/012909 on Jan. 24, 2014, now Pat. No. 10,856,749.
(Continued)

(51) Int. Cl.
*A61B 5/00* (2006.01)
*A61B 5/11* (2006.01)
(Continued)

(52) U.S. Cl.
CPC .......... *A61B 5/02416* (2013.01); *A61B 5/026* (2013.01); *A61B 5/14551* (2013.01);
(Continued)

(58) Field of Classification Search
None
See application file for complete search history.

(56) References Cited

U.S. PATENT DOCUMENTS

| 3,595,219 A | 7/1971 | Friedlander et al. |
| 3,769,974 A | 11/1973 | Smart et al. |

(Continued)

FOREIGN PATENT DOCUMENTS

| CA | 2 875 901 A1 | 12/2012 |
| CN | 1985751 A | 6/2007 |

(Continued)

OTHER PUBLICATIONS

"U.S. Army Fitness Training Handbook" by the Department of the Army, 2003, The Lyons Press, p. 17.
(Continued)

*Primary Examiner* — Colin T. Sakamoto
(74) *Attorney, Agent, or Firm* — Myers Bigel, P.A.

(57) ABSTRACT

A monitoring device includes a sensor band configured to be secured around an appendage of a subject, a sensing element secured to the sensor band, a second band configured to be secured to the appendage of the subject in adjacent, spaced-apart relationship with the sensor band, and at least one member connecting the sensor band and the second band. The sensor band has a first mass and the sensing element has a second mass that is less than the first mass. The sensing element is movably secured to the sensor band via a biasing element, and the biasing element is configured to urge the sensing element into contact with a portion of the appendage. The biasing element decouples motion of the sensor band from the sensing element, and the at least one member decouples motion between the sensor band and the second band.

33 Claims, 14 Drawing Sheets

Related U.S. Application Data

(60) Provisional application No. 61/757,504, filed on Jan. 28, 2013.

(51) Int. Cl.
*A61B 5/024* (2006.01)
*A61B 5/1455* (2006.01)
*A61B 5/026* (2006.01)

(52) U.S. Cl.
CPC .......... *A61B 5/14552* (2013.01); *A61B 5/681* (2013.01); *A61B 5/6817* (2013.01); *A61B 5/721* (2013.01); *A61B 5/11* (2013.01); *A61B 2562/0219* (2013.01)

(56) References Cited

U.S. PATENT DOCUMENTS

| | | | |
|---|---|---|---|
| 4,240,882 A | 12/1980 | Ang et al. | |
| 4,331,154 A | 5/1982 | Broadwater et al. | |
| 4,438,772 A | 3/1984 | Slavin | |
| 4,491,760 A | 1/1985 | Linvill | |
| 4,521,499 A | 6/1985 | Switzer | |
| 4,541,905 A | 9/1985 | Kuwana et al. | |
| 4,592,807 A | 6/1986 | Switzer | |
| 4,655,225 A | 4/1987 | Dahne et al. | |
| 4,830,014 A | 5/1989 | Goodman et al. | |
| 4,882,492 A | 11/1989 | Schlager | |
| 4,896,676 A | 1/1990 | Sasaki | |
| 4,928,704 A | 5/1990 | Hardt | |
| 4,957,109 A | 9/1990 | Groeger et al. | |
| 5,002,060 A | 3/1991 | Nedivi | |
| 5,022,970 A | 6/1991 | Cook et al. | |
| 5,025,791 A * | 6/1991 | Niwa | A61B 5/14552 600/324 |
| 5,050,612 A * | 9/1991 | Matsumura | A61M 5/14248 600/483 |
| 5,079,421 A | 1/1992 | Knudson et al. | |
| 5,080,098 A | 1/1992 | Willett et al. | |
| 5,086,229 A | 2/1992 | Rosenthal et al. | |
| 5,143,078 A | 9/1992 | Mather et al. | |
| 5,226,417 A | 7/1993 | Swedlow et al. | |
| 5,237,994 A | 8/1993 | Goldberger | |
| 5,348,002 A | 9/1994 | Caro | |
| 5,377,100 A | 12/1994 | Pope et al. | |
| 5,437,651 A | 8/1995 | Todd et al. | |
| 5,482,036 A | 1/1996 | Diab et al. | |
| 5,492,129 A | 2/1996 | Greenberger | |
| 5,499,301 A | 3/1996 | Sudo et al. | |
| 5,581,648 A | 12/1996 | Sahagen | |
| 5,596,987 A | 1/1997 | Chance | |
| 5,662,104 A | 9/1997 | Fuse et al. | |
| 5,662,117 A | 9/1997 | Bittman | |
| 5,666,952 A | 9/1997 | Fuse et al. | |
| 5,673,692 A | 10/1997 | Schulze et al. | |
| 5,697,374 A | 12/1997 | Odagiri et al. | |
| 5,711,308 A | 1/1998 | Singer | |
| 5,725,480 A | 3/1998 | Oosta et al. | |
| 5,743,260 A | 4/1998 | Chung et al. | |
| 5,779,631 A | 7/1998 | Chance | |
| 5,797,841 A | 8/1998 | Delonzor et al. | |
| 5,807,114 A | 9/1998 | Hodges et al. | |
| 5,807,267 A | 9/1998 | Bryars et al. | |
| 5,853,005 A | 12/1998 | Scanlon | |
| 5,904,654 A | 5/1999 | Wohltmann et al. | |
| 5,906,582 A * | 5/1999 | Kondo | A61B 5/222 600/500 |
| 5,938,593 A | 8/1999 | Ouellette | |
| 5,964,701 A | 10/1999 | Asada et al. | |
| 5,971,931 A | 10/1999 | Raff | |
| 5,974,338 A | 10/1999 | Asano et al. | |
| 5,980,472 A | 11/1999 | Seyl | |
| 5,995,858 A | 11/1999 | Kinast | |
| 6,004,274 A | 12/1999 | Nolan et al. | |
| 6,013,007 A | 1/2000 | Root et al. | |
| 6,023,541 A | 2/2000 | Merchant et al. | |
| 6,030,342 A | 2/2000 | Amano et al. | |
| 6,045,511 A | 4/2000 | Ott et al. | |
| 6,067,006 A | 5/2000 | O'Brien | |
| 6,070,093 A | 5/2000 | Oosta et al. | |
| 6,078,829 A | 6/2000 | Uchida et al. | |
| 6,080,110 A | 6/2000 | Thorgersen | |
| 6,081,742 A | 6/2000 | Amano et al. | |
| 6,186,145 B1 | 2/2001 | Brown | |
| 6,198,394 B1 | 3/2001 | Jacobsen et al. | |
| 6,198,951 B1 | 3/2001 | Kosuda et al. | |
| 6,205,354 B1 | 3/2001 | Gellermann et al. | |
| 6,231,519 B1 | 5/2001 | Blants et al. | |
| 6,283,915 B1 | 9/2001 | Aceti et al. | |
| 6,285,816 B1 | 9/2001 | Anderson et al. | |
| 6,289,230 B1 | 9/2001 | Chaiken et al. | |
| 6,298,314 B1 | 10/2001 | Blackadar et al. | |
| 6,332,868 B1 | 12/2001 | Sato et al. | |
| 6,358,216 B1 | 3/2002 | Kraus et al. | |
| 6,361,660 B1 | 3/2002 | Goldstein | |
| 6,371,925 B1 | 4/2002 | Imai et al. | |
| 6,374,129 B1 | 4/2002 | Chin et al. | |
| 6,415,167 B1 | 7/2002 | Blank et al. | |
| 6,443,890 B1 | 9/2002 | Schulze et al. | |
| 6,444,474 B1 | 9/2002 | Thomas et al. | |
| 6,454,718 B1 | 9/2002 | Clift | |
| 6,458,080 B1 | 10/2002 | Brown et al. | |
| 6,470,893 B1 | 10/2002 | Boesen | |
| 6,513,532 B2 | 2/2003 | Mault et al. | |
| 6,514,278 B1 | 2/2003 | Hibst et al. | |
| 6,527,711 B1 | 3/2003 | Stivoric et al. | |
| 6,527,712 B1 | 3/2003 | Brown et al. | |
| 6,529,754 B2 | 3/2003 | Kondo | |
| 6,534,012 B1 | 3/2003 | Hazen et al. | |
| 6,556,852 B1 | 4/2003 | Schulze et al. | |
| 6,569,094 B2 | 5/2003 | Suzuki et al. | |
| 6,571,117 B1 | 5/2003 | Marbach | |
| 6,605,038 B1 | 8/2003 | Teller et al. | |
| 6,616,613 B1 | 9/2003 | Goodman | |
| 6,631,196 B1 | 10/2003 | Taenzer et al. | |
| 6,647,378 B2 | 11/2003 | Kindo | |
| 6,656,116 B2 | 12/2003 | Kim et al. | |
| 6,676,597 B2 | 1/2004 | Guenst et al. | |
| 6,694,180 B1 | 2/2004 | Boesen | |
| 6,745,061 B1 | 6/2004 | Hicks et al. | |
| 6,748,254 B2 | 6/2004 | O'Neil et al. | |
| 6,760,610 B2 | 7/2004 | Tschupp et al. | |
| 6,783,501 B2 | 8/2004 | Takahashi et al. | |
| 6,808,473 B2 | 10/2004 | Hisano et al. | |
| 6,810,987 B1 | 11/2004 | Dekalb | |
| 6,859,658 B1 | 2/2005 | Krug | |
| 6,893,396 B2 | 5/2005 | Schulze et al. | |
| 6,941,239 B2 | 9/2005 | Unuma et al. | |
| 6,953,435 B2 | 10/2005 | Kondo et al. | |
| 6,996,427 B2 | 2/2006 | Ali et al. | |
| 6,997,879 B1 | 2/2006 | Turcott | |
| 7,018,338 B2 | 3/2006 | Vetter et al. | |
| 7,024,369 B1 | 4/2006 | Brown et al. | |
| 7,030,359 B2 | 4/2006 | Römhild | |
| 7,034,694 B2 | 4/2006 | Yamaguchi et al. | |
| 7,039,454 B1 | 5/2006 | Kaga et al. | |
| 7,041,062 B2 | 5/2006 | Friedrichs et al. | |
| 7,043,287 B1 | 5/2006 | Khalil et al. | |
| 7,054,674 B2 | 5/2006 | Cane et al. | |
| 7,088,234 B2 | 8/2006 | Naito et al. | |
| 7,107,088 B2 | 9/2006 | Aceti | |
| 7,113,815 B2 | 9/2006 | O'Neil et al. | |
| 7,117,032 B2 | 10/2006 | Childre et al. | |
| 7,163,512 B1 | 1/2007 | Childre et al. | |
| 7,175,601 B2 | 2/2007 | Verjus et al. | |
| 7,190,986 B1 | 3/2007 | Hannula et al. | |
| 7,209,775 B2 | 4/2007 | Bae et al. | |
| 7,217,224 B2 | 5/2007 | Thomas | |
| 7,252,639 B2 | 8/2007 | Kimura et al. | |
| 7,263,396 B2 | 8/2007 | Chen et al. | |
| 7,289,837 B2 | 10/2007 | Mannheimer et al. | |
| 7,336,982 B2 | 2/2008 | Yoo et al. | |
| 7,341,559 B2 | 3/2008 | Schultz et al. | |
| 7,376,451 B2 | 5/2008 | Mahony et al. | |

(56) References Cited

U.S. PATENT DOCUMENTS

| | | |
|---|---|---|
| 7,470,234 B1 | 12/2008 | Elhag et al. |
| 7,483,730 B2 | 1/2009 | Diab et al. |
| 7,486,988 B2 | 2/2009 | Goodall et al. |
| 7,507,207 B2 | 3/2009 | Sakai et al. |
| 7,519,327 B2 | 4/2009 | White |
| 7,526,327 B2 | 4/2009 | Blondeau et al. |
| 7,583,994 B2 | 9/2009 | Scholz |
| 7,625,285 B2 | 12/2009 | Breving |
| 7,652,569 B2 | 1/2010 | Kiff et al. |
| 7,689,437 B1 | 3/2010 | Teller et al. |
| 7,695,440 B2 | 4/2010 | Kondo et al. |
| 7,725,147 B2 | 5/2010 | Li et al. |
| 7,756,559 B2 | 7/2010 | Abreu |
| 7,843,325 B2 | 11/2010 | Otto |
| 7,894,869 B2 | 2/2011 | Hoarau |
| 7,914,468 B2 | 3/2011 | Shalon et al. |
| 7,991,448 B2 | 8/2011 | Edgar et al. |
| 7,998,079 B2 | 8/2011 | Nagai et al. |
| 8,050,728 B2 | 11/2011 | Al-Ali et al. |
| 8,055,319 B2 | 11/2011 | Oh et al. |
| 8,055,330 B2 | 11/2011 | Egozi |
| 8,059,924 B1 | 11/2011 | Letant et al. |
| 8,130,105 B2 | 3/2012 | Al-Ali et al. |
| 8,137,270 B2 | 3/2012 | Keenan et al. |
| 8,157,730 B2 | 4/2012 | LeBoeuf et al. |
| 8,172,459 B2 | 5/2012 | Abreu |
| 8,175,670 B2 | 5/2012 | Baker, Jr. et al. |
| 8,204,730 B2 | 6/2012 | Liu et al. |
| 8,204,786 B2 | 6/2012 | LeBoeuf et al. |
| 8,233,955 B2 | 7/2012 | Al-Ali et al. |
| 8,251,903 B2 | 8/2012 | LeBoeuf et al. |
| 8,255,027 B2 | 8/2012 | Al-Ali et al. |
| 8,255,029 B2 | 8/2012 | Addison et al. |
| 8,303,512 B2 | 11/2012 | Kosuda et al. |
| 8,320,982 B2 | 11/2012 | LeBoeuf et al. |
| 8,323,982 B2 | 12/2012 | LeBoeuf et al. |
| 8,328,420 B2 | 12/2012 | Abreu |
| 8,416,959 B2 | 4/2013 | Lott et al. |
| 8,491,492 B2 | 7/2013 | Shinar et al. |
| 8,504,679 B2 | 8/2013 | Spire et al. |
| 8,506,524 B2 | 8/2013 | Graskov et al. |
| 8,512,242 B2 | 8/2013 | LeBoeuf et al. |
| 8,647,270 B2 | 2/2014 | LeBoeuf et al. |
| 8,652,040 B2 | 2/2014 | LeBoeuf et al. |
| 8,652,409 B2 | 2/2014 | LeBoeuf et al. |
| 8,679,008 B2 | 3/2014 | Hughes et al. |
| 8,700,111 B2 | 4/2014 | LeBoeuf et al. |
| 8,702,607 B2 | 4/2014 | LeBoeuf et al. |
| 8,730,048 B2 | 5/2014 | Shen et al. |
| 8,788,002 B2 | 7/2014 | LeBoeuf et al. |
| 8,886,269 B2 | 11/2014 | LeBoeuf et al. |
| 8,888,701 B2 | 11/2014 | LeBoeuf et al. |
| 8,923,941 B2 | 12/2014 | LeBoeuf et al. |
| 8,929,965 B2 | 1/2015 | LeBoeuf et al. |
| 8,929,966 B2 | 1/2015 | LeBoeuf et al. |
| 8,934,952 B2 | 1/2015 | LeBoeuf et al. |
| 8,942,776 B2 | 1/2015 | LeBoeuf et al. |
| 8,961,415 B2 | 2/2015 | LeBoeuf et al. |
| 9,005,129 B2 | 4/2015 | Venkatraman et al. |
| 2001/0049471 A1 | 12/2001 | Suzuki et al. |
| 2002/0035340 A1 | 3/2002 | Fraden et al. |
| 2002/0143242 A1 | 10/2002 | Nemirovski |
| 2002/0156386 A1 | 10/2002 | Dardik et al. |
| 2002/0156654 A1 | 10/2002 | Roe et al. |
| 2002/0186137 A1 | 12/2002 | Skardon |
| 2002/0188210 A1 | 12/2002 | Aizawa |
| 2002/0194002 A1 | 12/2002 | Petrushin |
| 2003/0002705 A1 | 1/2003 | Boesen |
| 2003/0007631 A1 | 1/2003 | Bolognesi et al. |
| 2003/0045785 A1 | 3/2003 | Diab et al. |
| 2003/0050563 A1 | 3/2003 | Suribhotla et al. |
| 2003/0064712 A1 | 4/2003 | Gaston et al. |
| 2003/0065257 A1 | 4/2003 | Mault et al. |
| 2003/0083583 A1 | 5/2003 | Kovtun et al. |
| 2003/0109030 A1 | 6/2003 | Uchida et al. |
| 2003/0181795 A1 | 9/2003 | Suzuki et al. |
| 2003/0212336 A1 | 11/2003 | Lee et al. |
| 2003/0220584 A1 | 11/2003 | Honeyager et al. |
| 2003/0222268 A1 | 12/2003 | Yocom et al. |
| 2004/0004547 A1 | 1/2004 | Appelt et al. |
| 2004/0022700 A1 | 2/2004 | Kim et al. |
| 2004/0030581 A1 | 2/2004 | Leven |
| 2004/0034289 A1 | 2/2004 | Teller et al. |
| 2004/0034293 A1 | 2/2004 | Kimball |
| 2004/0054291 A1 | 3/2004 | Schulz et al. |
| 2004/0075677 A1 | 4/2004 | Loyall et al. |
| 2004/0077934 A1 | 4/2004 | Massad |
| 2004/0082842 A1 | 4/2004 | Lumba et al. |
| 2004/0103146 A1 | 5/2004 | Park |
| 2004/0117204 A1 | 6/2004 | Mazar et al. |
| 2004/0120844 A1 | 6/2004 | Tribelsky et al. |
| 2004/0122294 A1 | 6/2004 | Hatlestad et al. |
| 2004/0122702 A1 | 6/2004 | Sabol et al. |
| 2004/0133081 A1 | 7/2004 | Teller |
| 2004/0133123 A1 | 7/2004 | Leonhardt et al. |
| 2004/0135571 A1 | 7/2004 | Uutela et al. |
| 2004/0138578 A1 | 7/2004 | Pineda et al. |
| 2004/0186390 A1 | 9/2004 | Ross et al. |
| 2004/0219056 A1 | 11/2004 | Tribelsky et al. |
| 2004/0220488 A1 | 11/2004 | Vyshedskiy et al. |
| 2004/0225207 A1 | 11/2004 | Bae et al. |
| 2004/0228494 A1 | 11/2004 | Smith |
| 2004/0242976 A1 | 12/2004 | Abreu |
| 2005/0004458 A1 | 1/2005 | Kanayama et al. |
| 2005/0027216 A1 | 2/2005 | Guillemaud et al. |
| 2005/0030540 A1 | 2/2005 | Thornton |
| 2005/0033200 A1 | 2/2005 | Soehren et al. |
| 2005/0038349 A1 | 2/2005 | Choi et al. |
| 2005/0043600 A1 | 2/2005 | Diab et al. |
| 2005/0043630 A1 | 2/2005 | Buchert et al. |
| 2005/0058456 A1 | 3/2005 | Yoo |
| 2005/0059870 A1 | 3/2005 | Aceti |
| 2005/0070809 A1 | 3/2005 | Acres |
| 2005/0084666 A1 | 4/2005 | Pong et al. |
| 2005/0101845 A1 | 5/2005 | Nihtila |
| 2005/0101872 A1 | 5/2005 | Sattler et al. |
| 2005/0113167 A1 | 5/2005 | Buchner et al. |
| 2005/0113656 A1 | 5/2005 | Chance |
| 2005/0113703 A1 | 5/2005 | Farringdon et al. |
| 2005/0116820 A1 | 6/2005 | Goldreich |
| 2005/0119833 A1 | 6/2005 | Nanikashvili |
| 2005/0148883 A1 | 7/2005 | Boesen |
| 2005/0154264 A1 | 7/2005 | Lecompte et al. |
| 2005/0177034 A1 | 8/2005 | Beaumont |
| 2005/0187448 A1 | 8/2005 | Petersen et al. |
| 2005/0187453 A1 | 8/2005 | Petersen et al. |
| 2005/0192515 A1 | 9/2005 | Givens et al. |
| 2005/0196009 A1 | 9/2005 | Boesen |
| 2005/0203349 A1 | 9/2005 | Nanikashvili |
| 2005/0203357 A1 | 9/2005 | Debreczeny et al. |
| 2005/0209516 A1 | 9/2005 | Fraden |
| 2005/0222487 A1 | 10/2005 | Miller et al. |
| 2005/0222903 A1 | 10/2005 | Buchheit et al. |
| 2005/0228244 A1 | 10/2005 | Banet |
| 2005/0228299 A1 | 10/2005 | Banet |
| 2005/0234351 A1 | 10/2005 | Nishii et al. |
| 2005/0240087 A1 | 10/2005 | Keenan et al. |
| 2005/0258816 A1 | 11/2005 | Zen et al. |
| 2005/0259811 A1 | 11/2005 | Kimm et al. |
| 2006/0009685 A1 | 1/2006 | Finarov et al. |
| 2006/0012567 A1 | 1/2006 | Sicklinger |
| 2006/0063993 A1 | 3/2006 | Yu et al. |
| 2006/0064037 A1 | 3/2006 | Shalon et al. |
| 2006/0084878 A1 | 4/2006 | Banet et al. |
| 2006/0084879 A1 | 4/2006 | Nazarian et al. |
| 2006/0122520 A1 | 6/2006 | Banet et al. |
| 2006/0123885 A1 | 6/2006 | Yates et al. |
| 2006/0140425 A1 | 6/2006 | Berg et al. |
| 2006/0142665 A1 | 6/2006 | Garay et al. |
| 2006/0202816 A1 | 9/2006 | Crump et al. |
| 2006/0205083 A1 | 9/2006 | Zhao |
| 2006/0210058 A1 | 9/2006 | Kock et al. |
| 2006/0211922 A1 | 9/2006 | Al-Ali et al. |
| 2006/0211924 A1 | 9/2006 | Dalke et al. |

(56) References Cited

U.S. PATENT DOCUMENTS

| | | |
|---|---|---|
| 2006/0217598 A1 | 9/2006 | Miyajima et al. |
| 2006/0224059 A1 | 10/2006 | Swedlow et al. |
| 2006/0240558 A1 | 10/2006 | Zhao |
| 2006/0246342 A1 | 11/2006 | MacPhee |
| 2006/0251277 A1 | 11/2006 | Cho |
| 2006/0251334 A1 | 11/2006 | Oba et al. |
| 2006/0252999 A1 | 11/2006 | Devaul et al. |
| 2006/0264730 A1 | 11/2006 | Stivoric et al. |
| 2006/0292533 A1 | 12/2006 | Selod |
| 2006/0293921 A1 | 12/2006 | McCarthy et al. |
| 2007/0004449 A1 | 1/2007 | Sham |
| 2007/0004969 A1 | 1/2007 | Kong et al. |
| 2007/0015992 A1 | 1/2007 | Filkins et al. |
| 2007/0021206 A1 | 1/2007 | Sunnen |
| 2007/0027367 A1 | 2/2007 | Oliver et al. |
| 2007/0027399 A1 | 2/2007 | Chou |
| 2007/0036383 A1 | 2/2007 | Romero |
| 2007/0050215 A1 | 3/2007 | Kil et al. |
| 2007/0060800 A1 | 3/2007 | Drinan et al. |
| 2007/0063850 A1 | 3/2007 | Devaul et al. |
| 2007/0082789 A1 | 4/2007 | Nissila et al. |
| 2007/0083092 A1 | 4/2007 | Rippo et al. |
| 2007/0083095 A1 | 4/2007 | Rippo et al. |
| 2007/0088221 A1 | 4/2007 | Stahmann |
| 2007/0093702 A1 | 4/2007 | Yu et al. |
| 2007/0106167 A1 | 5/2007 | Kinast |
| 2007/0112273 A1 | 5/2007 | Rogers |
| 2007/0112598 A1 | 5/2007 | Heckerman et al. |
| 2007/0116314 A1 | 5/2007 | Grilliot et al. |
| 2007/0118043 A1 | 5/2007 | Oliver et al. |
| 2007/0165872 A1 | 7/2007 | Bridger et al. |
| 2007/0167850 A1 | 7/2007 | Russell et al. |
| 2007/0191718 A1 | 8/2007 | Nakamura |
| 2007/0197878 A1 | 8/2007 | Shklarski |
| 2007/0197881 A1 | 8/2007 | Wolf et al. |
| 2007/0213020 A1 | 9/2007 | Novac |
| 2007/0230714 A1 | 10/2007 | Armstrong |
| 2007/0233403 A1 | 10/2007 | Alwan et al. |
| 2007/0260129 A1 | 11/2007 | Chin |
| 2007/0265097 A1 | 11/2007 | Havukainen |
| 2007/0270667 A1 | 11/2007 | Coppi et al. |
| 2007/0270671 A1 | 11/2007 | Gal |
| 2007/0293781 A1 | 12/2007 | Sims et al. |
| 2007/0299330 A1 | 12/2007 | Couronne et al. |
| 2008/0004536 A1 | 1/2008 | Baxi et al. |
| 2008/0015424 A1 | 1/2008 | Bernreuter |
| 2008/0039731 A1* | 2/2008 | McCombie ........ A61B 5/02255 600/485 |
| 2008/0076972 A1 | 3/2008 | Dorogusker et al. |
| 2008/0081963 A1* | 4/2008 | Naghavi ............. A61B 5/6806 600/301 |
| 2008/0086533 A1 | 4/2008 | Neuhauser et al. |
| 2008/0096726 A1 | 4/2008 | Riley et al. |
| 2008/0114220 A1 | 5/2008 | Banet et al. |
| 2008/0132798 A1 | 6/2008 | Hong et al. |
| 2008/0141301 A1 | 6/2008 | Azzaro et al. |
| 2008/0146892 A1* | 6/2008 | LeBoeuf ............ A61B 5/02055 600/300 |
| 2008/0154098 A1 | 6/2008 | Morris et al. |
| 2008/0154105 A1 | 6/2008 | Lemay |
| 2008/0165017 A1 | 7/2008 | Schwartz |
| 2008/0170600 A1 | 7/2008 | Sattler et al. |
| 2008/0171945 A1 | 7/2008 | Dotter |
| 2008/0177162 A1 | 7/2008 | Bae et al. |
| 2008/0200774 A1 | 8/2008 | Luo |
| 2008/0203144 A1 | 8/2008 | Kim |
| 2008/0221461 A1 | 9/2008 | Zhou et al. |
| 2008/0249393 A1 | 10/2008 | Finarov et al. |
| 2008/0249594 A1 | 10/2008 | Dietrich |
| 2008/0287752 A1 | 11/2008 | Stroetz et al. |
| 2009/0005662 A1 | 1/2009 | Petersen et al. |
| 2009/0006457 A1 | 1/2009 | Stivoric et al. |
| 2009/0010461 A1 | 1/2009 | Klinghult et al. |
| 2009/0030350 A1 | 1/2009 | Yang et al. |
| 2009/0054751 A1 | 2/2009 | Babashan et al. |
| 2009/0054752 A1 | 2/2009 | Jonnalagadda et al. |
| 2009/0069645 A1 | 3/2009 | Nielsen et al. |
| 2009/0082994 A1 | 3/2009 | Schuler et al. |
| 2009/0088611 A1 | 4/2009 | Buschmann |
| 2009/0093687 A1 | 4/2009 | Telfort et al. |
| 2009/0105548 A1 | 4/2009 | Bart |
| 2009/0105556 A1 | 4/2009 | Fricke et al. |
| 2009/0131761 A1 | 5/2009 | Moroney, III et al. |
| 2009/0131764 A1 | 5/2009 | Lee et al. |
| 2009/0175456 A1 | 7/2009 | Johnson |
| 2009/0177097 A1 | 7/2009 | Ma et al. |
| 2009/0214060 A1 | 8/2009 | Chuang et al. |
| 2009/0221888 A1 | 9/2009 | Wijesiriwardana |
| 2009/0227853 A1 | 9/2009 | Wijesiriwardana |
| 2009/0240125 A1 | 9/2009 | Such et al. |
| 2009/0253992 A1 | 10/2009 | Van Der Loo |
| 2009/0253996 A1 | 10/2009 | Lee et al. |
| 2009/0264711 A1 | 10/2009 | Schuler et al. |
| 2009/0270698 A1 | 10/2009 | Shioi et al. |
| 2009/0287067 A1 | 11/2009 | Dorogusker et al. |
| 2009/0299215 A1 | 12/2009 | Zhang |
| 2010/0004517 A1 | 1/2010 | Bryenton et al. |
| 2010/0022861 A1 | 1/2010 | Cinbis et al. |
| 2010/0045663 A1 | 2/2010 | Chen et al. |
| 2010/0100013 A1 | 4/2010 | Hu et al. |
| 2010/0113948 A1 | 5/2010 | Yang et al. |
| 2010/0168531 A1 | 7/2010 | Shaltis et al. |
| 2010/0172522 A1 | 7/2010 | Mooring et al. |
| 2010/0179389 A1 | 7/2010 | Moroney et al. |
| 2010/0185105 A1 | 7/2010 | Baldinger |
| 2010/0217098 A1 | 8/2010 | LeBoeuf et al. |
| 2010/0217099 A1 | 8/2010 | LeBoeuf et al. |
| 2010/0217100 A1 | 8/2010 | LeBoeuf |
| 2010/0217103 A1 | 8/2010 | Abdul-Hafiz et al. |
| 2010/0222655 A1 | 9/2010 | Starr et al. |
| 2010/0228315 A1 | 9/2010 | Nielsen |
| 2010/0234714 A1 | 9/2010 | Mercier et al. |
| 2010/0268056 A1 | 10/2010 | Picard et al. |
| 2010/0274100 A1 | 10/2010 | Behar et al. |
| 2010/0274109 A1 | 10/2010 | Hu et al. |
| 2010/0292589 A1* | 11/2010 | Goodman .......... A61B 5/02438 600/500 |
| 2010/0298653 A1 | 11/2010 | McCombie et al. |
| 2011/0002881 A1 | 2/2011 | Slyke et al. |
| 2011/0028813 A1 | 2/2011 | Watson et al. |
| 2011/0081037 A1 | 4/2011 | Oh et al. |
| 2011/0098112 A1 | 4/2011 | LeBoeuf |
| 2011/0105869 A1 | 5/2011 | Wilson et al. |
| 2011/0112382 A1 | 5/2011 | Li et al. |
| 2011/0130638 A1 | 6/2011 | Raridan, Jr. |
| 2011/0142371 A1 | 6/2011 | King et al. |
| 2011/0242531 A1* | 10/2011 | Natan .................. G01N 21/658 356/300 |
| 2011/0242532 A1* | 10/2011 | McKenna ................ D04H 3/14 356/319 |
| 2011/0288379 A1 | 11/2011 | Wu |
| 2012/0030547 A1 | 2/2012 | Raptis et al. |
| 2012/0095303 A1 | 4/2012 | He |
| 2012/0116231 A1 | 5/2012 | Liao et al. |
| 2012/0150052 A1 | 6/2012 | Buchheim et al. |
| 2012/0156933 A1 | 6/2012 | Kreger et al. |
| 2012/0179011 A1 | 7/2012 | Moon et al. |
| 2012/0197093 A1* | 8/2012 | LeBoeuf ................ G16H 40/63 600/301 |
| 2012/0203081 A1 | 8/2012 | LeBoeuf et al. |
| 2012/0226111 A1 | 9/2012 | LeBoeuf et al. |
| 2012/0226112 A1 | 9/2012 | LeBoeuf et al. |
| 2012/0277548 A1 | 11/2012 | Burton |
| 2012/0283577 A1 | 11/2012 | LeBoeuf et al. |
| 2012/0296184 A1 | 11/2012 | LeBoeuf et al. |
| 2013/0053661 A1 | 2/2013 | Alberth et al. |
| 2013/0072765 A1 | 3/2013 | Kahn et al. |
| 2013/0245387 A1 | 9/2013 | Patel |
| 2013/0336495 A1 | 12/2013 | Burgett et al. |
| 2014/0012105 A1 | 1/2014 | LeBoeuf et al. |
| 2014/0051940 A1 | 2/2014 | Messerschmidt |
| 2014/0051948 A1 | 2/2014 | LeBoeuf et al. |
| 2014/0052567 A1 | 2/2014 | Bhardwaj et al. |
| 2014/0058220 A1 | 2/2014 | LeBoeuf et al. |

(56) References Cited

U.S. PATENT DOCUMENTS

| | | |
|---|---|---|
| 2014/0073486 A1 | 3/2014 | Ahmed et al. |
| 2014/0088433 A1 | 3/2014 | Shan |
| 2014/0094663 A1 | 4/2014 | LeBoeuf et al. |
| 2014/0100432 A1 | 4/2014 | Golda et al. |
| 2014/0114147 A1 | 4/2014 | Romesburg et al. |
| 2014/0127996 A1 | 5/2014 | Park et al. |
| 2014/0128690 A1 | 5/2014 | LeBoeuf et al. |
| 2014/0128751 A1* | 5/2014 | Donaldson ............... A61B 5/11 600/490 |
| 2014/0135596 A1 | 5/2014 | LeBoeuf et al. |
| 2014/0140567 A1 | 5/2014 | LeBoeuf et al. |
| 2014/0187885 A1 | 7/2014 | Kreuzer |
| 2014/0219467 A1 | 8/2014 | Kurtz |
| 2014/0235967 A1 | 8/2014 | LeBoeuf et al. |
| 2014/0235968 A1 | 8/2014 | LeBoeuf et al. |
| 2014/0236531 A1 | 8/2014 | Carter |
| 2014/0243617 A1 | 8/2014 | LeBoeuf et al. |
| 2014/0243620 A1 | 8/2014 | LeBoeuf et al. |
| 2014/0275852 A1 | 9/2014 | Hong et al. |
| 2014/0275855 A1 | 9/2014 | LeBoeuf et al. |
| 2014/0287833 A1 | 9/2014 | LeBoeuf et al. |
| 2014/0288396 A1 | 9/2014 | LeBoeuf et al. |
| 2014/0288436 A1 | 9/2014 | Venkatraman et al. |
| 2014/0323829 A1 | 10/2014 | LeBoeuf et al. |
| 2014/0323830 A1 | 10/2014 | LeBoeuf et al. |
| 2014/0323880 A1 | 10/2014 | Ahmed et al. |
| 2014/0378844 A1 | 12/2014 | Fei |
| 2014/0378853 A1* | 12/2014 | McKinney ......... A61B 5/02438 600/509 |
| 2015/0011898 A1 | 1/2015 | Romesburg |
| 2015/0018636 A1 | 1/2015 | Romesburg |
| 2015/0031967 A1 | 1/2015 | LeBoeuf et al. |
| 2015/0032009 A1 | 1/2015 | LeBoeuf et al. |
| 2015/0057967 A1 | 2/2015 | Albinali |
| 2015/0190085 A1 | 7/2015 | Nathan et al. |
| 2015/0250396 A1 | 9/2015 | Ahmed et al. |
| 2015/0265217 A1 | 9/2015 | Penders et al. |
| 2015/0289820 A1 | 10/2015 | Miller et al. |
| 2015/0342481 A1 | 12/2015 | Liu et al. |
| 2015/0366509 A1 | 12/2015 | Romesburg |
| 2016/0022220 A1 | 1/2016 | Lee et al. |
| 2016/0029964 A1 | 2/2016 | LeBoeuf et al. |
| 2016/0094899 A1 | 3/2016 | Aumer et al. |
| 2016/0287108 A1 | 10/2016 | Wei et al. |
| 2017/0034615 A1 | 2/2017 | Mankodi et al. |

FOREIGN PATENT DOCUMENTS

| | | |
|---|---|---|
| CN | 101212927 A | 7/2008 |
| CN | 201438747 U | 4/2010 |
| CN | 102046085 A | 5/2011 |
| CN | 102185963 A | 9/2011 |
| DE | 3910749 A1 | 10/1990 |
| EP | 1 297 784 A1 | 4/2003 |
| EP | 1 480 278 A2 | 11/2004 |
| EP | 2 077 091 A2 | 7/2009 |
| EP | 2 182 839 B1 | 10/2011 |
| GB | 2 408 209 A | 5/2005 |
| GB | 2 411 719 A | 9/2005 |
| JP | 7-241279 | 9/1995 |
| JP | 9-253062 | 9/1997 |
| JP | 9-299342 | 11/1997 |
| JP | 2000-116611 | 4/2000 |
| JP | 2001-025462 | 1/2001 |
| JP | 2003-159221 | 6/2003 |
| JP | 2004-513750 A | 5/2004 |
| JP | 2004-283523 | 10/2004 |
| JP | 2007-044203 | 2/2007 |
| JP | 2007-185348 | 7/2007 |
| JP | 2008-43515 A | 2/2008 |
| JP | 2008-136556 A | 6/2008 |
| JP | 2008-279061 A | 11/2008 |
| JP | 2009-153664 A | 7/2009 |
| JP | 2010-526646 | 8/2010 |
| JP | 2014-068733 A | 4/2014 |
| KR | 20-0204510 Y1 | 11/2000 |
| WO | WO 00/24064 | 4/2000 |
| WO | WO 00/047108 A1 | 8/2000 |
| WO | WO 01/08552 A1 | 2/2001 |
| WO | WO 2002/017782 A2 | 3/2002 |
| WO | WO 2005/010568 A2 | 2/2005 |
| WO | WO 2005/020121 A1 | 3/2005 |
| WO | WO 2005/110238 A1 | 11/2005 |
| WO | WO 2006/009830 A2 | 1/2006 |
| WO | WO 2006/067690 A2 | 6/2006 |
| WO | WO 2007/012931 A2 | 2/2007 |
| WO | WO 2007/023426 A2 | 3/2007 |
| WO | WO 2007/038432 A2 | 4/2007 |
| WO | WO 2007/053146 A1 | 5/2007 |
| WO | WO 2008/141306 A2 | 11/2008 |
| WO | WO 2011/094875 A1 | 8/2011 |
| WO | 2012168388 A2 | 12/2012 |
| WO | WO 2013/019494 A2 | 2/2013 |
| WO | WO 2013/038296 A1 | 3/2013 |
| WO | WO 2013/109389 A1 | 7/2013 |
| WO | WO 2013/109390 A1 | 7/2013 |
| WO | WO 2014/092932 A1 | 6/2014 |
| WO | WO 2015/128226 A1 | 9/2015 |

OTHER PUBLICATIONS

"Warfighter Physiological and Environmental Monitoring: A Study for the U.S. Army Research Institute in Environmental Medicine and the Soldier Systems Center", Massachusetts Institute of Technology Lincoln Laboratory, Final Report, Nov. 1, 2004, prepared for the U.S. Army under Air Force Contract F19628-00-C-0002; approved for public release.

Anpo et al. "Photocatalytic Reduction of $Co_2$ With $H_2O$ on Titanium Oxides Anchored within Micropores of Zeolites: Effects of the Structure of the Active Sites and the Addition of Pt" *J. Phys. Chem. B*, 101:2632-2636 (1997).

Bârsan et al. "Understanding the fundamental principles of metal oxide based gas sensors; the example of CO sensing with $SnO_2$ sensors in the presence of humidity" *Journal of Physics: Condensed Matter* 15:R813-R839 (2003).

Bott "Electrochemistry of Semiconductors" *Current Separations* 17(3):87-91 (1998).

Colligan, M. J. et al. in "The psychological effects of indoor air pollution", Bulletin of the New York Academy of Medicine, vol. 57, No. 10, Dec. 1981, p. 1014-1026.

De Paula Santos, U. et al., in "Effects of air pollution on blood pressure and heart rate variability: a panel study of vehicular traffic controllers in the city of Sao Paulo, Brazil", European Heart Journal (2005) 26, 193-200.

Ebert, T et al., "Influence of Hydration Status on Thermoregulation and Cycling Hill Climbing," Med. Sci. Sport Exerc. vol. 39, No. 2, pp. 323-329, 2007.

Edmison et al., "E-Textile Based Automatic Activity Diary for Medical Annotation and Analysis," Proc. BSN 2006 Int. Workshop Wearable Implantable Body Sensor Netw. (2006), pp. 131-145, Apr. 3-5, 2006.

European Search Report corresponding to European Application No. 07862660.3 dated Apr. 25, 2012; 7 pages.

Falkner et al., "Cardiovascular response to mental stress in normal adolescents with hypertensive parents Hemodynamics and mental stress in adolescents," *Hypertension* 1979, 1:23-30.

Fitrainer "The Only Trainer You Need"; http://itami.com; Downloaded Feb. 26, 2010; ©2008 FiTriainer™; 2 pages.

Fleming et al., "A Comparison of Signal Processing Techniques for the Extraction of Breathing Rate from the Photopethysmorgram," World Academy of Science, Engineering and Technology, vol. 30, Oct. 2007, pp. 276-280.

Geladas et al., "Effect of cold air inhalation on core temperature in exercising subjects under stress," The American Physiological Society, pp. 2381-2387, 1988.

Gibbs et al., "Reducing Motion Artifact Reduction for Wearable Sensors Using MEMS Accelerometers for Active Noise Cancellation," 2005 American Control Conference, Jun. 8-10, 2005, Portland, OR, USA, pp. 1581-1586.

(56) References Cited

OTHER PUBLICATIONS

Gold, D.R. et al. in "Ambient Pollution and Heart Rate Variability", Circulation 2000, 101:1267-1273.
International Search Report corresponding to International Patent Application No. PCT/US2012/046446, dated Jan. 14, 2013, 3 pages.
International Search Report and Written Opinion of the International Searching Authority, corresponding to PCT/US2012/0948079, dated Oct. 9, 2012.
International Search Report and Written Opinion of the International Searching Authority, corresponding to PCT/US2007/025114, dated May 13, 2008.
International Search Report Corresponding to International Application No. PCT/US2012/022634, dated Aug. 22, 2012, 9 pages.
Maomao et al., "Mobile Context-Aware Game for the Next Generation," $2^{nd}$ International Conference on Application and Development of Computer Games ADCOG 2003, p. 78-81.
Martins et al. "Zinc oxide as an ozone sensor" *Journal of Applied Physics* 96(3):1398-1408 (2004).
Maughan, R.J., "Impact of mild dehydration on wellness and on exercise performance," European Journal of Clinical Nutrition, 57, Suppl. 2, pp. S19-S23, 2003.
Maughan et al., "Exercise, Heat, Hydration and the Brain," Journal of the American College of Nutrition, vol. 26, No. 5, p. 604S-612S, 2007.
Mostardi, R., et al., "The effect of increased body temperature due to exercise on the heart rate and the maximal aerobic power," Europ. J. Appl. Physiol, 33, pp. 237-245, 1974.
Nakajima et al., "Monitoring of heart and respiratory rates by photoplethyusmography using a digital filtering technique," Med. Eng. Phys., vol. 18, No. 5, Jul. 1996, pp. 365-372.
Notification Concerning Transmittal of International Preliminary Report on Patentability, PCT/US2014/012909, dated Jul. 28, 2015.
Notification of Transmittal of the International Search Report and Written Opinion of the International Search Authority dated Jul. 30, 2010 by the Korean Intellectual Property Office for corresponding International Application No. PCT/US2010/021936.
Notification of Transmittal of the International Search Report and Written Opinion of the International Search Authority dated Aug. 26, 2010 by the Korean Intellectual Property Office for corresponding International Application No. PCT/US2010/021629.
Notification of Transmittal of the International Search Report and the Written Opinion of the International Search Authority dated Sep. 16, 2010 by the Korean Intellectual Property Office for corresponding International Application No. PCT/US2010/024922.
Notification of Transmittal of the International Search Report and the Written Opinion of the International Search Authority dated Sep. 27, 2010 by the Korean Intellectual Property Office for corresponding International Application No. PCT/US2010/025216.
Notification of Transmittal of The International Search Report and The Written Opinion of the International Searching Authority, or the Declaration corresponding to International Application No. PCT/US2013/070271; dated Feb. 26, 2014; 13 pages.
Saladin et al. "Photosynthesis of $CH_4$ at a $TiO_2$ Surface from Gaseous $H_2O$ and $CO_2$" *J. Chem. Soc., Chem. Commun.* 533-534 (1995).
Shorten et al., "Acute effect of environmental temperature during exercise on subsequent energy intake in active men," Am. J Clin. Nutr. 90, pp. 1215-1221, 2009.
Skubal et al. "Detection and identification of gaseous organics using a $TiO_2$ sensor" *Journal of Photochemistry and Photobiology A: Chemistry* 148:103-108 (2002).
Skubal et al. "Monitoring the Electrical Response of Photoinduced Organic Oxideation on $TiO_2$ Surfaces" Manuscript submitted Oct. 2000 to SPIE Intl. Symposium on Environment & Industrial Sensing, Boston, MA, Nov. 5-8, 2000, sponsored by SPIE, 10 pp.
Thompson, M.W., "Cardiovascular drift and critical core temperature: factors limiting endurance performance in the heat?" J. Exerc. Sci. Fit, vol. 4, No. 1, pp. 15-24, 2006.
Wood et al., "Active Motion Artifact Reduction for Wearable Sensors Using Laguerre Expansion and Signal Separator," Proceedings of the 2005 IEEE Engineering in Medicine and Biology, $27^{th}$ Annual Conference, Shanghai, China, Sep. 1-4, 2005, pp. 3571-3574.
Zhang et al. "Development of Chemical Oxygen Demand On-Line Monitoring System Based on a Photoelectrochemical Degradation Principle" *Environ. Sci. Technol.*, 40(7):2363-2368 (2006).
European Search Report, EP Application No. 13863449.8, dated Oct. 19, 2015, 3 pages.
European Search Report, EP Application No. 14743615.8, dated Oct. 12, 2015, 3 pages.
European Search Report, EP Application No. 14743839.4, dated Oct. 12, 2015, 3 pages.
Gibbs et al., "Reducing Motion Artifact in Wearable Bio-Sensors Using MEMS Accelerometers for Active Noise Cancellation," 2005 American Control Conference, Jun. 8-10, 2005, Portland, OR, USA, pp. 1581-1586.
International Preliminary Report on Patentability, PCT/US2014/012940, dated Jun. 17, 2015, 23 pages.
International Search Report and Written Opinion of the International Searching Authority, corresponding to International Patent Application No. PCT/US2014/012940, dated Oct. 16, 2014, 13 pages.
International Search Report corresponding to International Patent Application No. PCT/US2014/012909, dated May 13, 2014, 3 pages.
Notification of Transmittal of the International Search Report and the Written Opinion of the International Searching Authority, or the Declaration, PCT/US2015/014562, dated Oct. 28, 2015.
Notification of Transmittal of the International Search Report and the Written Opinion of the International Searching Authority, or the Declaration, PCT/US2015/042636, dated Oct. 29, 2015.
Notification of Transmittal of the International Search Report and the Written Opinion of the International Searching Authority, or the Declaration, PCT/US2015/042015, dated Oct. 29, 2015.
Notification of Transmittal of the International Search Report and the Written Opinion of the International Searching Authority, or the Declaration, PCT/US2015/042035, dated Oct. 29, 2015.
Wood et al., "Active Motion Artifact Reduction for Wearable Sensors Using Laguerre Expansion and Signal Separation," Proceedings of the 2005 IEEE Engineering in Medicine and Biology, $27^{th}$ Annual Conference, Shanghai, China, Sep. 1-4, 2005, pp. 3571-3574.
Notification of Transmittal of the International Search Report and the Written Opinion of the International Searching Authority, or the Declaration, PCT/US2015/046079, dated Dec. 29, 2015.
Communication pursuant to Article 94(3) EPC, European Patent Application No. 13863449.8, dated Nov. 5, 2015, 7 pages.
Communication pursuant to Article 94(3) EPC, European Patent Application No. 14743615.8, dated Dec. 23, 2015, 7 pages.
Communication pursuant to Article 94(3) EPC, European Patent Application No. 14743839.4, dated Dec. 23, 2015, 6 pages.
Communication pursuant to Article 94(3) EPC, European Patent Application No. 12820308.0, dated Feb. 3, 2016, 5 pages.
Notification of Transmittal of the International Search Report and Written Opinion of the International Search Authority dated May 26, 2016 by the Korean Intellectual Property Office for corresponding International Application No. PCT/US2016/019126.
Notification of Transmittal of the International Search Report and Written Opinion of the International Search Authority dated May 26, 2016 by the Korean Intellectual Property Office for corresponding International Application No. PCT/US2016/019132.
Asada, et al., "Mobile Monitoring with Wearable Photoplethysmographic Biosensors," IEEE Engineering in Medicine and Biology Magazine, May/Jun. 2003, pp. 28-40.
Bifulco et al., "Bluetooth Portable Device for Continuous ECG and Patient Motion Monitoring During Daily Life," Medicon 2007, IFMBE Proceedings 16, 2007, pp. 369-372.
Brodersen et al., "In-Ear Acquisition of Vital Signs Discloses New Chances for Preventive Continuous Cardiovascular Monitoring," 4th International Workshop on Wearable and Implantable Body Sensor Networks (BSN 2007), vol. 13 of the series IFMBE Proceedings, pp. 189-194.

(56) References Cited

OTHER PUBLICATIONS

Celka et al., "Motion Resistant Earphone Located Infrared based Heart Rate Measurement Device," Proceedings of the Second IASTED International Conference on Biomedical Engineering, Feb. 16-18, 2004, Innsbruck, Austria, pp. 582-585.
Communication Pursuant to Article 94(3) EPC, EP 12 739 502.8, dated Jul. 19, 2016, 7 pages.
Communication Pursuant to Article 94(3) EPC, EP 14 743 615.8, dated Jul. 19, 2016, 7 pages.
Communication Pursuant to Article 94(3) EPC, EP 14 743 839.4, dated Jul. 20, 2016, 5 pages.
Comtois et al., "A Wearable Wireless Reflectance Pulse Oximeter for Remote Triage Applications," 2006 IEEE, pp. 53-54.
Comtois, Gary, W., "Implementation of Accelerometer-Based Adaptive Noise Cancellation in a Wireless Wearable Pulse Oximeter Platform for Remote Physiological Monitoring and Triage," Thesis, Worcester Polytechnic Institute, Aug. 31, 2007, 149 pages.
Duun et al., "A Novel Ring Shaped Photodiode for Reflectance Pulse Oximetry in Wireless Applications," IEEE Sensors 2007 Conference, pp. 596-599.
Geun et al., "Measurement Site and Applied Pressure Consideration in Wrist Photoplethysmography," The $23^{rd}$ International Technical Conference on Circuits/Systems, Computersand Communications, 2008, pp. 1129-1132.
Gibbs et al., "Active motion artifact cancellation for wearable health monitoring sensors using collocated MEMS accelerometers," Smart Structures and Materials, 2005: Sensors and Smart Structures Technologies for Civil, Mechanical, and Aerospace Systems, Proc, of SPIE, vol. 5765, pp. 811-819.
Haahr et al., "A Wearable "Electronic Patch" for Wireless Continuous Monitoring of Chronically Diseased Patients," Proceedings of the $5^{th}$ International Workshop on Wearable and Implantable Body Sensor Networks, in conjunction with The $5^{th}$ International Summer School and Symposium on Medical Devices and Biosensors, The Chinese University of Hong Kong, HKSAR, China, Jun. 1-3, 2008, pp. 66-70.
Jiang, Honghui, "Motion-Artifact Resistant Design of Photoplethysmograph Ring Sensor for Driver Monitoring," Thesis, Massachusetts Institute of Technology, Feb. 2004, 62 pages.
Kuzmina et al., "Compact multi-functional skin spectrometry set-up," Advanced Optical Materials, Technologies, and Devices, Proc, of SPIE, vol. 6596, 2007, p. 65960T-1 to 65960T-6.
Lee et al., "Respiratory Rate Detection Algorithms by Photoplethysmography Signal Processing," $30^{th}$ Annual International IEEE EMBS Conference, Vancouver, British Columbia, Canada, Aug. 20-24, 2008, pp. 1140-1143.
Lindberg et al., "Monitoring of respiratory and heart rates using a fibre-optic sensor," Med Biol Eng Comput, Sep. 1992, vol. 30, No. 5, pp. 533-537.
Luprano, Jean, "Sensors and Parameter Extraction by Wearable Systems: Present Situation and Future," pHealth 2008, May 21, 2008, 29 pages.
Lygouras et al., "Optical-Fiber Finger Photo-Plethysmograph Using Digital Techniques," IEEE Sensors Journal, vol. 2, No. 1, Feb. 2002, pp. 20-25.
Maguire et al., "The Design and Clinical Use of a Reflective Brachial Photoplethysmograph," Technical Report NUIM/SS/—/ 2002/04, Submitted Apr. 2002, Signals and Systems Research Group, National University of Ireland, Maynooth, Co. Kildare, Ireland, 13 pages.
Mendelson et al., "Measurement Site and Photodetector Size Considerations in Optimizing Power Consumption of a Wearable Reflectance Pulse Oximeter," Proceedings of the $25^{th}$ Annual International Conference of the IEEE EMBS, Cancun, Mexico, Sep. 17-21, 2003, pp. 3016-3019.
Mendelson et al., "Noninvasive Pulse Oximetry Utilizing Skin Reflectance Photoplethysmography," IEEE Transactions on Biomedical Engineering, vol. 35, No. 10, Oct. 1988, pp. 798-805.

Poh et al., "Motion Tolerant Magnetic Earring Sensor and Wireless Earpiece for Wearable Photoplethysmography," IEEE Transactions on Information Technology in Biomedicine, vol. 14, No. 3, May 2010, pp. 786-794.
Renevey et al., "Wrist-Located Pulse Detection Using IR Signals, Activity and Nonlinear Artifact Cancellation," IEEE EMBS, 2001, 4 pages.
Rhee et al., "Artifact-Resistant Power-Efficient Design of Finger-Ring Plethysmographic Sensors," IEEE Transactions on Biomedical Engineering, vol. 48, No. 7, Jul. 2001, pp. 795-805.
Shaltis, Phillip Andrew, Analysis and Validation of an Artifact Resistant Design for Oxygen Saturation Measurement Using Photo Plethysmographic Ring Sensors, Thesis, Massachusetts Institute of Technology, Jun. 2004, 103 pages.
Shin et al., "A Novel Headset with a Transmissive PPG Sensor for Heart Rate Measurement," ICBME 2008, Proceedings 23, 2009, pp. 519-522.
Spigulis et al., "Wearable wireless photoplethysmography sensors," Proc. of SPIE, vol. 6991, 2008, p. 69912O-1 to 69912O-7.
Takatani et al., "Optical Oximetry Sensors for Whole Blood and Tissue," IEEE Engineering in Medicine and Biology, Jun./Jul. 1994, pp. 347-357.
Vogel et al., "A System for Assessing Motion Artifacts in the Signal of a Micro-Optic In-Ear Vital Signs Sensor," $30^{th}$ Annual International IEEE EMBS Conference, Vancouver, British Columbia, Canada, Aug. 20-24, 2008.
Vogel et al., "In-Ear Heart Rate Monitoring Using a Micro-Optic Reflective Sensor," Proceedings of the $29^{th}$ Annual International Conference of the IEEE EMBS Cite Internationale, Lyon, France, Aug. 23-26, 2007, pp. 1375-1378.
Wang et al., "Multichannel Reflective PPG Earpiece Sensor With Passive Motion Cancellation," IEEE Transactions on Biomedical Circuits and Systems, vol. 1, No. 4, Dec. 2007, pp. 235-241.
Wang et al., "Reflective Photoplethysmograph Earpiece Sensor for Ubiquitous Heart Rate Monitoring," $4^{th}$ International Workshop on Wearable and Implantable Body Sensor Networks, 2007, vol. 13 of the series IFMBE Proceedings, pp. 179-183.
Wei et al. "A New Wristband Wearable Sensor Using Adaptive Reduction Filter to Reduce Motion Artifact," Proceedings of the $5^{th}$ International Conference on Information Technology and Application in Biomedicine, in conjunction with The $2^{nd}$ International Symposium & Summer School on Biomedical and Health Engineering, Shenzhen, China, May 30-31, 2008, pp. 278-281.
Wood, Levi Benjamin, "Motion Artifact Reduction for Wearable Photoplethysmogram Sensors Using Micro Accelerometers and Laguerre Series Adaptive Filters," Thesis, Massachusetts Institute of Technology, Jun. 2008, 74 pages.
Han et al., "Artifacts in wearable photoplethysmographs during daily life motions and their reduction with least mean square based active noise cancellation method," Computers in Biology and Medicine, 42, 2012, pp. 387-393.
Extended European Search Report, EP Application No. 16164775.5, dated Sep. 13, 2016, 7 pages.
Notification of Transmittal of the International Search Report and the Written Opinion of the International Searching Authority, or the Declaration, PCT/US2016/041842, dated Oct. 21, 2016, 5 pages.
Notification of Transmittal of International Preliminary Report on Patentability, PCT/US2015/041562, dated Oct. 20, 2016, 14 pages.
Notification of Transmittal of International Preliminary Report on Patentability, PCT/US2015/042636, dated Oct. 20, 2016, 7 pages.
Notification of Transmittal of International Preliminary Report on Patentability, PCT/US2015/042015, dated Oct. 20, 2016, 10 pages.
Notification of Transmittal of International Preliminary Report on Patentability, PCT/US2015/042035, dated Oct. 20, 2016, 8 pages.
Notification of Transmittal of International Preliminary Report on Patentability, PCT/US2015/046079, dated Oct. 20, 2016, 10 pages.
Extended European Search Report, European Application No. 16184560. 7, dated Dec. 20, 2016, 9 pages.
Extended European Search Report, European Application No. 16183137. 5, dated Jan. 12, 2017, 12 pages.
Communication pursuant to Article 94(3) EPC, European Application No. 12 739 502.8, dated Nov. 30, 2016, 6 pages.

(56) References Cited

OTHER PUBLICATIONS

Notification of Transmittal of the International Search Report and the Written Opinion of the International Searching Authority, or the Declaration, PCT/US2016/046273, dated Nov. 25, 2016, 24 pages.
Notification of Transmittal of the International Search Report and the Written Opinion of the International Searching Authority, or the Declaration, PCT/US2016/058098, dated Jan. 10, 2017, 13 pages.
Communication pursuant to Article 94(3) EPC, European Application No. 14 743 615.8, dated Jan. 30, 2017, 5 pages.
Communication pursuant to Article 94(3) EPC, European Application No. 14 743 839.4, dated Jan. 30, 2017, 7 pages.
Chinese Office Action corresponding to Chinese Application No. 201480019033.9 dated May 10, 2017.
Communication pursuant to Article 94(3) EPC, EPO Application No. 14743839.4, dated Jul. 19, 2017, 5 pp.
Communication pursuant to Article 94(3) EPC, EPO Application No. 14743615.8, dated Jul. 26, 2017, 5 pp.
Third Office Action and English-language translation, Chinese Patent Application No. 201480018381.4, dated May 24, 2018, 20 pp.
Summons to attent oral proceedings pursuant to Rule 115(1) EPC, EP Application No. 14743615.8, dated Jan. 23, 2020, 10 pp.
"First Office Action and English language translation", CN Application No. 201910036179.9, dated Apr. 27, 2021, 7 pp.
"First Office Action and English language translation", CN Application No. 201910036198.1, dated May 18, 2021, 24 pp.
"First Office Action and English language translation", CN Application No. 201810556676.7, dated Aug. 10, 2020, 31 pp.
"Second Office Action and English language translation", CN Application No. 201810556676.7, dated Feb. 8, 2021, 6 pp.

\* cited by examiner

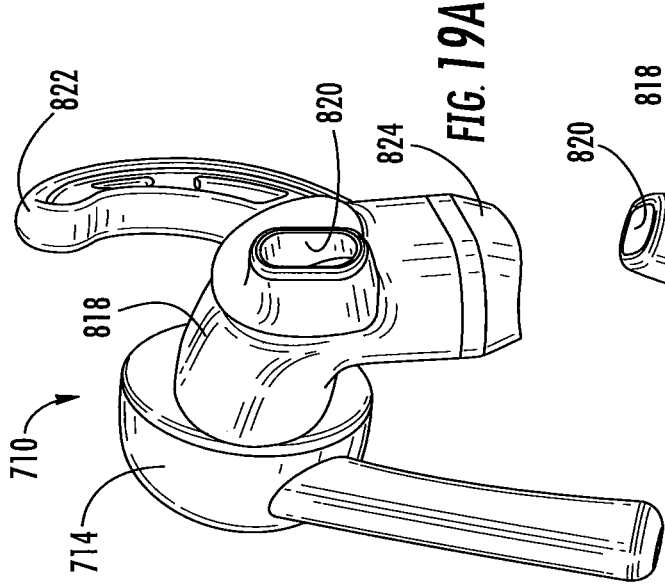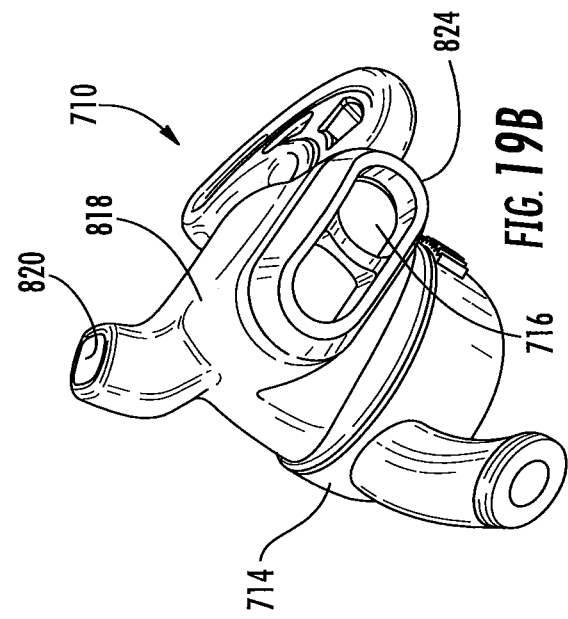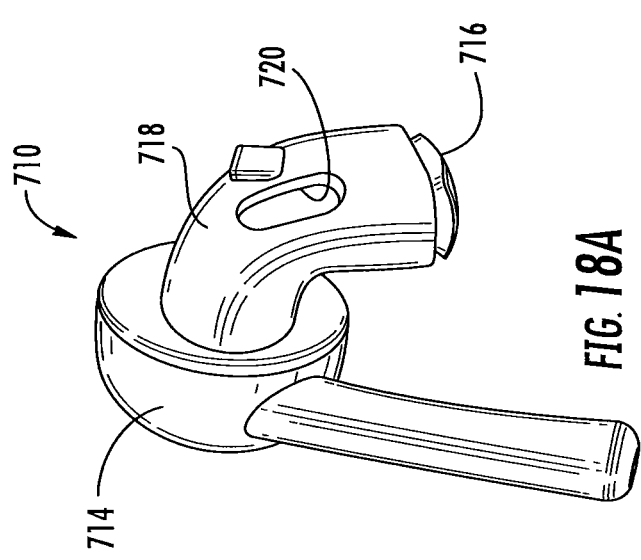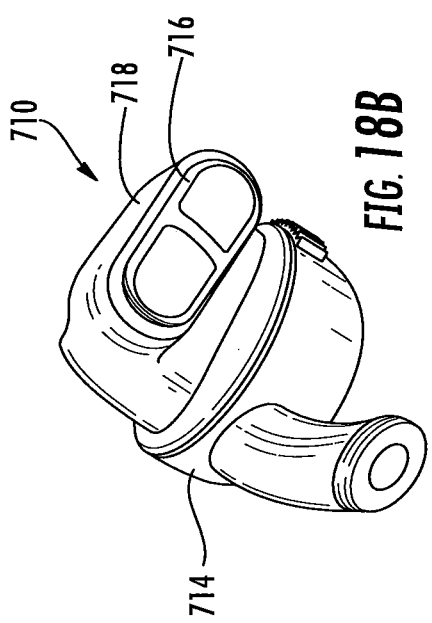

PHYSIOLOGICAL MONITORING DEVICES HAVING SENSING ELEMENTS DECOUPLED FROM BODY MOTION

RELATED APPLICATION

This application is a continuation application of pending U.S. patent application Ser. No. 14/761,462, filed Jul. 16, 2015, which is a 35 U.S.C. § 371 national stage application of PCT Application No. PCT/US2014/012909, filed on Jan. 24, 2014, which claims the benefit of and priority to U.S. Provisional Patent Application No. 61/757,504 filed Jan. 28, 2013, the disclosures of which are incorporated herein by reference as if set forth in their entireties. The above-referenced PCT International Application was published in the English language as International Publication No. WO 2014/116924 on Jul. 31, 2014.

FIELD OF THE INVENTION

The present invention relates generally to monitoring devices and, more particularly, to monitoring devices for measuring physiological information.

BACKGROUND OF THE INVENTION

Photoplethysmography (PPG) is based upon shining light into the human body and measuring how the scattered light intensity changes with each pulse of blood flow. The scattered light intensity will change in time with respect to changes in blood flow or blood opacity associated with heart beats, breaths, blood oxygen level ($SpO_2$), and the like. Such a sensing methodology may require the magnitude of light energy reaching the volume of flesh being interrogated to be steady and consistent so that small changes in the quantity of scattered photons can be attributed to varying blood flow. If the incidental and scattered photon count magnitude changes due to light coupling variation between the source or detector and the skin surface, then the signal of interest can be difficult to ascertain due to large photon count variability caused by loss or variation of optical coupling. Changes in the surface area (and volume) of skin being impacted with photons, or varying skin surface curvature reflecting significant portions of the photons may also significantly impact optical coupling efficiency. Physical activity, such a walking, cycling, running, etc., may cause motion artifacts in the optical scatter signal from the body, and time-varying changes in photon intensity due to motion artifacts may swamp-out time-varying changes in photon intensity due to blood flow changes. Each of these changes in optical coupling can affect the photonic interrogation count by a large percent of the total photon count and diminish the quality of the signal of interest; with lower probability of obtaining accurate values of desired data.

An earphone is a good choice for incorporation of a photoplethysmograph device because it is a form factor that individuals are familiar with, it is a device that is commonly worn for long periods of time, and it frequently is used during exercise which is a time when individuals may benefit most from having accurate heart rate data (or other physiological data). Unfortunately, incorporation of a photoplethysmograph device into an earphone poses several challenges. For example, earphones may be uncomfortable to wear for long periods of time, particularly if they deform the ear surface. Moreover, human ear anatomy may vary significantly from person to person, so finding an earbud form that will fit comfortably in many ears may pose significant challenges. In addition, earbuds made for vigorous physical activity typically incorporate an elastomeric surface and/or elastomeric features to function as springs that dampen earbud acceleration within the ear. Although, these features may facilitate retention of an earbud within an ear during high acceleration and impact modalities, they do not adequately address optical skin coupling requirements needed to achieve quality photoplethysmography.

Conventional photoplethysmography devices, as illustrated for example in FIGS. 1A-1C, typically suffer from reduced skin coupling as a result of subject motion. For example, most conventional photoplethysmography devices use a spring to clip the sensor onto either an earlobe (FIG. 1A) or a fingertip (FIG. 1B). Unfortunately, these conventional devices tend to have a large mass and may not maintain consistent skin contact when subjected to large accelerations, such as when a subject is exercising.

A conventional earbud device that performs photoplethysmography in the ear is the MX-D100 player from Perception Digital of Wanchai, Hong Kong (www.perceptiondigital-.com). This earbud device, illustrated in FIG. 1C and indicated as 10, incorporates a spring 12 to improve PPG signal quality. However, the spring 12 forcibly presses the entire earbud 10 within the ear E of a subject to minimize motion of the entire earbud 10. There are several drawbacks to the device 10 of FIG. 1C. For example, the source/sensor module is coupled to the entire earbud mass and, as such, may experience larger translation distances resulting in greater signal variability when the ear undergoes accelerations. In addition, because the earbud 10 is held in place with one primary spring force direction, significant discomfort can be experienced by the end user. Moreover, the earbud motion is only constrained in one direction due to the single spring force direction.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

Some embodiments of the present invention put a module containing one or more energy emitters and energy detectors on a biasing element, such as an elastomeric arm that decouples earbud vibration from sensor vibration. Moreover, the biasing element urges the sensor module into intimate contact with the skin surface.

According to some embodiments of the present invention, a monitoring device includes a biasing element having opposite first and second end portions, and a sensing element attached to the biasing element second end portion. The monitoring device is configured to be attached to an ear of a subject such that the biasing element first end portion engages the ear at a first location and such that the sensing element is urged by the biasing member into contact with the ear at a second location. The sensing element includes at least one energy emitter configured to direct energy at a target region of the ear and at least one detector configured to detect an energy response signal from the target region or a region adjacent the target region. For example, the at least one energy emitter is configured to direct electromagnetic radiation, mechanical energy, acoustical energy, electrical energy, and/or thermal energy at the target region, and the at least one detector is configured to detect electromagnetic radiation, mechanical energy, acoustical energy, electrical energy, and/or thermal energy. In some embodiments, the at least one energy emitter comprises at least one optical emitter and the at least one detector comprises at least one optical detector.

In some embodiments of the present invention, the sensing element includes a surface having at least one window through which energy passes from the at least one energy emitter, and through which energy is collected by the at least one detector. The at least one window may include at least one opening. Moreover, the surface may be shaped to conform to a shape of a portion of the ear of a subject.

In some embodiments of the present invention, the sensing element may include a signal processor configured to receive and process signals produced by the at least one detector.

In some embodiments of the present invention, the biasing element may include a motion sensor that is configured to detect motion of the biasing element and/or sensing element. The motion sensor may be, for example, an inertial sensor, a piezoelectric sensor, an optical sensor, etc. In some embodiments, the motion sensor may be a photoplethysmography (PPG) sensor used for measuring blood flow.

According to other embodiments of the present invention, a monitoring device includes a biasing element having opposite first and second end portions, an earbud attached to the biasing element first end portion, and a sensing element attached to the biasing element second end portion. The earbud has a first mass, and the sensing element has a second mass that is less than the first mass. The biasing element is configured to urge the sensing element into contact with a portion of the ear when the earbud is inserted into the ear. In addition, the biasing element decouples motion of the earbud from the sensing element.

The sensing element includes at least one energy emitter configured to direct energy at a target region of the ear and at least one detector configured to detect an energy response signal from the target region and/or a region adjacent the target region. For example, the at least one energy emitter is configured to direct electromagnetic radiation, mechanical energy, acoustical energy, electrical energy, and/or thermal energy at the target region, and the at least one detector is configured to detect electromagnetic radiation, mechanical energy, acoustical energy, electrical energy, and/or thermal energy. In some embodiments, the at least one energy emitter comprises at least one optical emitter and the at least one detector comprises at least one optical detector.

In some embodiments, the earbud includes an optical emitter. A light guide having a distal end terminates adjacent a window in a surface of the sensing element. The light guide is in optical communication with the optical emitter and is configured to deliver light from the optical emitter into an ear region of the subject via the light guide distal end. In some embodiments, the light guide extends from the optical emitter to the sensing element at least partially through the biasing element.

In some embodiments, the earbud includes an optical detector. A light guide having a distal end terminates adjacent a window in a surface of the sensing element. The light guide is in optical communication with the optical detector and is configured to collect light from an ear region of the subject via the light guide distal end and deliver collected light to the optical detector. In some embodiments, the light guide extends from the optical detector to the sensing element at least partially through the biasing element.

In some embodiments of the present invention, the sensing element includes a surface having at least one window through which energy passes from the at least one energy emitter, and through which energy is collected by the at least one detector. The at least one window may include at least one opening. In addition, the surface may be shaped to conform to a shape of a portion of the ear of a subject.

In some embodiments of the present invention, the sensing element may include a signal processor configured to receive and process signals produced by the at least one detector.

In some embodiments of the present invention, the biasing element may include a motion sensor that is configured to detect motion of the biasing element and/or sensing element. The motion sensor may be, for example, an inertial sensor, a piezoelectric sensor, etc.

In some embodiments of the present invention, a speaker is disposed within the earbud, and the earbud includes at least one aperture through which sound from the speaker can pass.

According to other embodiments of the present invention, a monitoring device includes a housing configured to be attached to an ear of a subject and a sensing element movably secured to the housing via a biasing element. The housing has a first mass, and the sensing element has a second mass that is less than the first mass. In some embodiments, the first mass is at least 1.25 times greater than the second mass. The biasing element is configured to urge the sensing element into contact with a portion of the ear, and decouples motion of the housing from the sensing element.

The sensing element includes at least one energy emitter configured to direct energy at a target region of the ear and at least one detector configured to detect an energy response signal from the target region or a region adjacent the target region. For example, the at least one energy emitter is configured to direct electromagnetic radiation, mechanical energy, acoustical energy, electrical energy, and/or thermal energy at the target region, and the at least one detector is configured to detect electromagnetic radiation, mechanical energy, acoustical energy, electrical energy, and/or thermal energy. In some embodiments, the at least one energy emitter comprises at least one optical emitter and the at least one detector comprises at least one optical detector.

In some embodiments, the biasing element includes a motion sensor configured to detect motion of the biasing element and/or sensing element.

In some embodiments, the biasing element comprises a flexible member that at least partially surrounds the sensing element. The flexible member comprises a compressible, resilient material, such as gel. In some embodiments, the monitoring device includes a speaker within the housing. A sound port is formed through the flexible member and housing so as to be in acoustical communication with the speaker.

Earbud monitoring devices, according to embodiments of the present invention, are advantageous over conventional monitoring devices for several reasons. One is comfort of fit. An earbud monitoring device according to embodiments of the present invention is comfortable and may provide more accurate biometrics than conventional earbuds. Moreover, by designing the sensor element as a separate body from the earbud, the earbud can be tailored for comfort. Another advantage is that by providing supplemental spring action on the sensor module an additional level of sensor to skin intimacy may be achieved. By decoupling the sensor module and earbud, less spring force (pressure) is needed to maintain sensor contact with the ear, thus resulting in greater comfort. A device where the sensor can stay in contact with the interrogation area of interest, even under extreme accelerations, may be able to continuously report data and offer the end-user a higher confidence level in the device's accuracy.

According to other embodiments of the present invention, a monitoring device includes a sensor band configured to be secured around an appendage of a subject, and a sensing element movably secured to the sensor band via a biasing element. The sensor band has a first mass, and the sensing element has a second mass that is less than the first mass. In some embodiments, the first mass is at least 1.25 times greater than the second mass. The biasing element is configured to urge the sensing element into contact with a portion of the appendage, and the biasing element decouples motion of the band from the sensing element.

The sensing element includes at least one energy emitter configured to direct energy at a target region of the body and at least one detector configured to detect an energy response signal from the target region or a region adjacent the target region. For example, the at least one energy emitter is configured to direct electromagnetic radiation, mechanical energy, acoustical energy, electrical energy, and/or thermal energy at the target region, and the at least one detector is configured to detect electromagnetic radiation, mechanical energy, acoustical energy, electrical energy, and/or thermal energy. In some embodiments, the at least one energy emitter comprises at least one optical emitter and the at least one detector comprises at least one optical detector. In some embodiments, the biasing element includes a motion sensor configured to detect motion of the biasing element and/or sensing element.

In some embodiments, the monitoring device includes a second band that is configured to be secured to the appendage of the subject in adjacent, spaced-apart relationship with the sensor band. At least one member or bridge connects the sensor band and second band together.

According to other embodiments of the present invention, a monitoring device includes a band that is configured to be secured around an appendage of a subject, wherein the band comprises an inner surface and an outer surface. A plurality of biasing elements extend radially outward from the inner surface in circumferential spaced-apart relationship and are configured to contact the appendage. A sensing element is secured to the band inner surface between two of the biasing elements. In some embodiments, the sensing element extends outwardly from the band inner surface such that the at least one energy emitter and at least one detector associated with the sensing element do not contact the appendage when the band is secured around the appendage. In other embodiments, the sensing element extends outwardly from the band inner surface such that the at least one energy emitter and at least one detector associated with the sensing element contact the appendage when the band is secured around the appendage.

The at least one energy emitter is configured to direct electromagnetic radiation, mechanical energy, acoustical energy, electrical energy, and/or thermal energy at the target region, and the at least one detector is configured to detect electromagnetic radiation, mechanical energy, acoustical energy, electrical energy, and/or thermal energy. In some embodiments, the at least one energy emitter comprises at least one optical emitter and the at least one detector comprises at least one optical detector.

According to other embodiments of the present invention, a monitoring device includes a band that is configured to be secured around an appendage of a subject and includes an inner surface and an outer surface. An elongated biasing element having opposite ends is secured circumferentially to the band inner surface such that the opposite ends are in adjacent, spaced-apart relationship. The biasing element comprises a surface that contacts the appendage when the band is secured around the appendage. A sensing element is secured to the band inner surface between the adjacent, spaced-apart biasing element ends.

The sensing element includes at least one energy emitter configured to direct energy at a target region of the appendage and at least one detector configured to detect an energy response signal from the target region or region adjacent to the target region. The at least one energy emitter is configured to direct electromagnetic radiation, mechanical energy, acoustical energy, electrical energy, and/or thermal energy at the target region, and the at least one detector is configured to detect electromagnetic radiation, mechanical energy, acoustical energy, electrical energy, and/or thermal energy. In some embodiments, the at least one energy emitter comprises at least one optical emitter and the at least one detector comprises at least one optical detector. In some embodiments, the sensing element includes a surface having at least one window through which energy passes from the at least one energy emitter, and through which energy is collected by the at least one detector.

In some embodiments, the sensing element extends outwardly from the band inner surface such that the at least one energy emitter and at least one detector associated with the sensing element do not contact the appendage when the band is secured around the appendage. In other embodiments, the sensing element extends outwardly from the band inner surface such that the at least one energy emitter and at least one detector associated with the sensing element contact the appendage when the band is secured around the appendage.

In some embodiments, one or more portions of the biasing element surface have a textured configuration, such as a plurality of raised bumps. The raised bumps may be arranged in an array and may have various shapes and sizes. In some embodiments, the plurality of raised bumps have alternating shapes.

Embodiments of the present invention utilize a sensing element as a distinct third body relative to a monitoring device and a body of a subject wearing the monitoring device. For example, if the monitoring device is an earbud configured to be secured within the ear of a subject, the ear of the subject is the first body, the earbud is the second body, and the sensing element or module is a distinct third body. As such, embodiments of the present invention provide several advantages over conventional monitoring devices. First, the mass of the sensing element, according to embodiments of the present invention, is reduced since the sensing element is decoupled from the earbud body. This lower mass may see smaller displacements as a result of ear, earbud or appendage accelerations, for example, as a result of subject motion. Second, a sensing element, according to embodiments of the present invention, can be shaped and presented to the interrogation surface of interest in a form tailored for optical coupling and not restricted by conventional forms, such as conventional earbud forms.

In addition, the effect of earbud cabling pulling on an earbud and possibly dislodging the sensor to skin contact can be minimized by having a biasing element, such as a spring, between the earbud and the sensor, according to embodiments of the present invention. By incorporating a biasing element between an earbud and sensor, fit within one or more portions of the concha of an ear can be achieved with an optimized earbud form, while fit between the sensor and interrogation surface can be optimized for photoplethysmography. Moreover, because any dampened system will have a lag in response to vibrational compensation, decoupling the sensor element from earbud motion allows the sensor response to be better tuned to managing small vibrational offsets; whereas, the earbud dampening structures are best designed to handle larger displacements inherent from a larger, heavier mass body with multiple ear contact points. The earbud makes larger amplitude acceleration compensations compared to the sensor element due to its larger mass. The secondary minor acceleration compensations of the sensor to ear surface (or appendage) movement may be significantly reduced as well as signal variation.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

The accompanying drawings, which form a part of the specification, illustrate various embodiments of the present invention. The drawings and description together serve to fully explain embodiments of the present invention.

FIGS. 18A-18B and 19A-19B are perspective views of a monitoring device having a compressible outer cover, or gel, at least partially surrounding a core monitoring device and configured to bias a sensing element in a desired region of the ear, according to some embodiments of the present invention.

DETAILED DESCRIPTION

Figure 1A:
FIG. 1A is a perspective view of a conventional photoplethysmography device attached to the ear of a person.
Figure 1B:
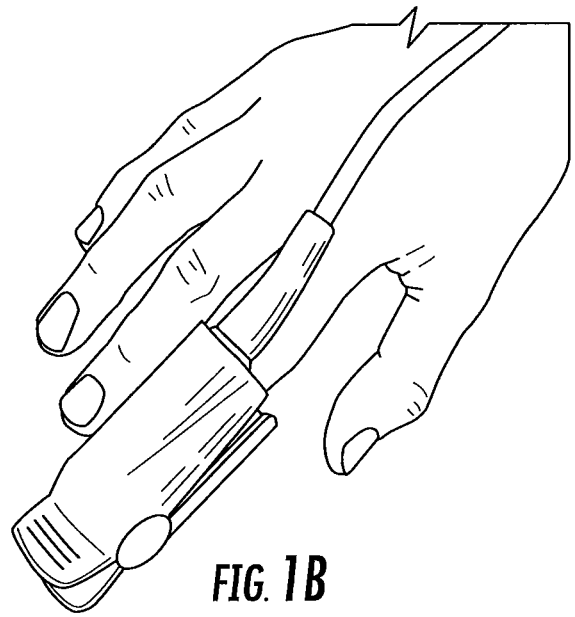
FIG. 1B is a perspective view of a conventional photoplethysmography device attached to a finger of a person.
Figure 1C:
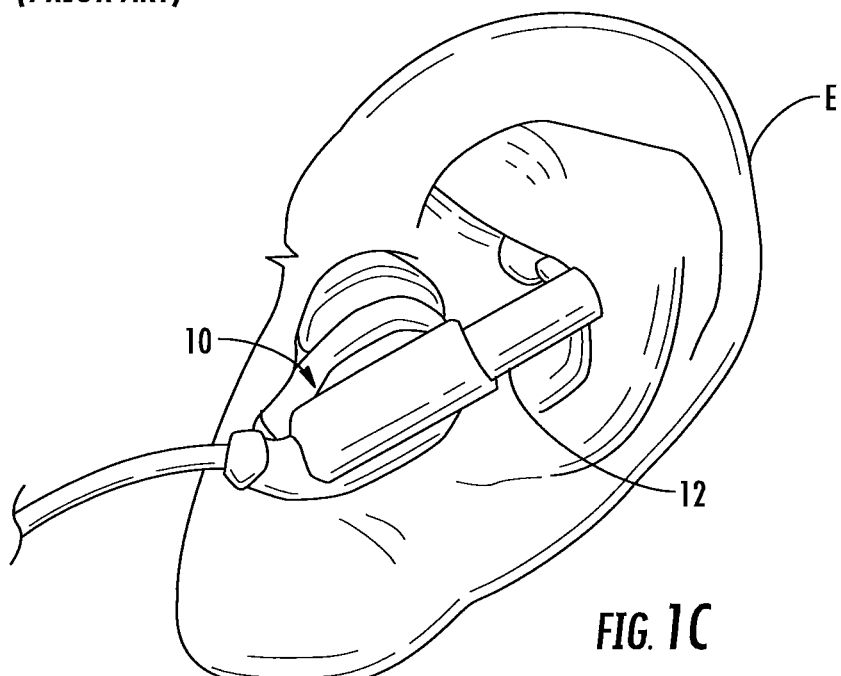
FIG. 1C illustrates a conventional photoplethysmography device attached to the ear of a person, and wherein a biasing element is utilized to retain the photoplethysmography device in the person's ear.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. Features described with respect to one figure or embodiment can be associated with another embodiment or figure although not specifically described or shown as such.

It will be understood that when a feature or element is referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that although the terms first and second are used herein to describe various features/elements, these features/elements should not be limited by these terms. These terms are only used to distinguish one feature/element from another feature/element. Thus, a first feature/element discussed below could be termed a second feature/element, and similarly, a second feature/element discussed below could be termed a first feature/element without departing from the teachings of the present invention. Like numbers refer to like elements throughout.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "about", as used herein with respect to a value or number, means that the value or number can vary by +/− twenty percent (20%).

The term "monitoring device" includes any type of device that may be attached to or near the ear or to an appendage of a user and may have various configurations, without limitation.

The term "real-time" is used to describe a process of sensing, processing, or transmitting information in a time frame which is equal to or shorter than the minimum timescale at which the information is needed. For example, the real-time monitoring of pulse rate may result in a single average pulse-rate measurement every minute, averaged over 30 seconds, because an instantaneous pulse rate is often useless to the end user. Typically, averaged physiological and environmental information is more relevant than instantaneous changes. Thus, in the context of the present invention, signals may sometimes be processed over several seconds, or even minutes, in order to generate a "real-time" response.

The term "monitoring" refers to the act of measuring, quantifying, qualifying, estimating, sensing, calculating, interpolating, extrapolating, inferring, deducing, or any combination of these actions. More generally, "monitoring" refers to a way of getting information via one or more sensing elements. For example, "blood health monitoring" includes monitoring blood gas levels, blood hydration, and metabolite/electrolyte levels.

The term "physiological" refers to matter or energy of or from the body of a creature (e.g., humans, animals, etc.). In embodiments of the present invention, the term "physiological" is intended to be used broadly, covering both physical and psychological matter and energy of or from the body of a creature. However, in some cases, the term "psychological" is called-out separately to emphasize aspects of physiology that are more closely tied to conscious or subconscious brain activity rather than the activity of other organs, tissues, or cells.

The term "body" refers to the body of a subject (human or animal) that may wear a monitoring device, according to embodiments of the present invention.

In the following figures, various monitoring devices will be illustrated and described for attachment to the ear or an appendage of the human body. However, it is to be understood that embodiments of the present invention are not limited to those worn by humans.

The ear is an ideal location for wearable health and environmental monitors. The ear is a relatively immobile platform that does not obstruct a person's movement or vision. Monitoring devices located at an ear have, for example, access to the inner-ear canal and tympanic membrane (for measuring core body temperature), muscle tissue (for monitoring muscle tension), the pinna, earlobe, and elsewhere (for monitoring blood gas levels), the region behind the ear (for measuring skin temperature and galvanic skin response), and the internal carotid artery (for measuring cardiopulmonary functioning), etc. The ear is also at or near the point of exposure to: environmental breathable toxicants of interest (volatile organic compounds, pollution, etc.; noise pollution experienced by the ear; and lighting conditions for the eye. Furthermore, as the ear canal is naturally designed for transmitting acoustical energy, the ear provides a good location for monitoring internal sounds, such as heartbeat, breathing rate, and mouth motion.

Optical coupling into the blood vessels of the ear may vary between individuals. As used herein, the term "coupling" refers to the interaction or communication between excitation energy (such as light) entering a region and the region itself. For example, one form of optical coupling may be the interaction between excitation light generated from within a light-guiding earbud and the blood vessels of the ear. In one embodiment, this interaction may involve excitation light entering the ear region and scattering from a blood vessel in the ear such that the temporal change in intensity of scattered light is proportional to a temporal change in blood flow within the blood vessel. Another form of optical coupling may be the interaction between excitation light generated by an optical emitter within an earbud and the light-guiding region of the earbud. Thus, an earbud with integrated light-guiding capabilities, wherein light can be guided to multiple and/or select regions along the earbud, can assure that each individual wearing the earbud will generate an optical signal related to blood flow through the blood vessels. Optical coupling of light to a particular ear region of one person may not yield photoplethysmographic signals for each person. Therefore, coupling light to multiple regions may assure that at least one blood-vessel-rich region will be interrogated for each person wearing the light-guiding earbud. Coupling multiple regions of the ear to light may also be accomplished by diffusing light from a light source within the earbud.

Figure 2A:
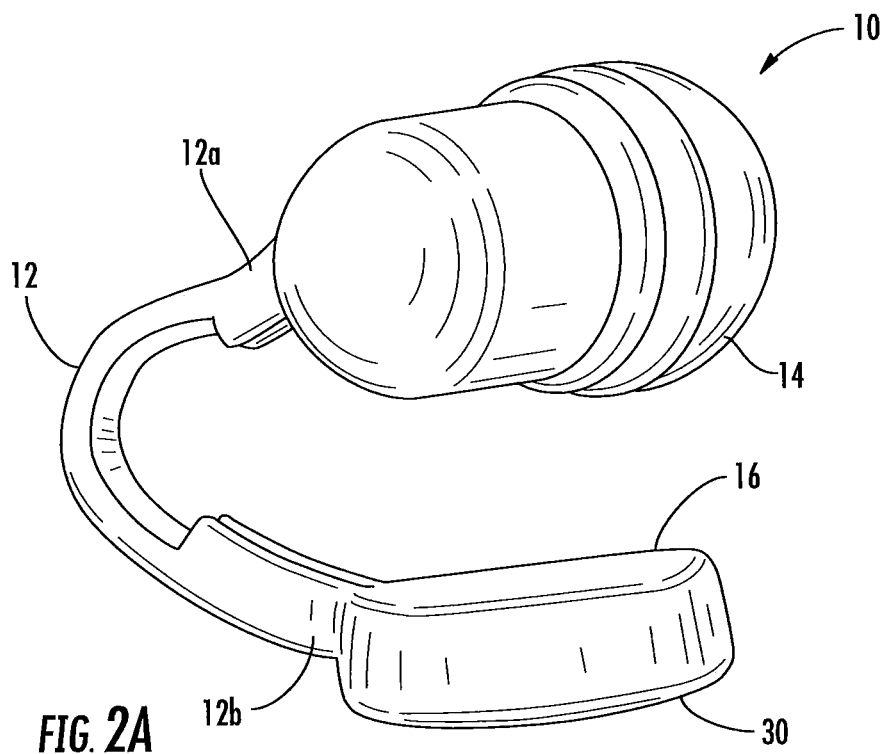
FIGS. 2A-2C are perspective views of a monitoring device having an earbud and a sensing element attached to the earbud via a biasing member, according to some embodiments of the present invention, and wherein the biasing member is configured to decouple motion of the earbud from the sensing element.
Figure 2B:
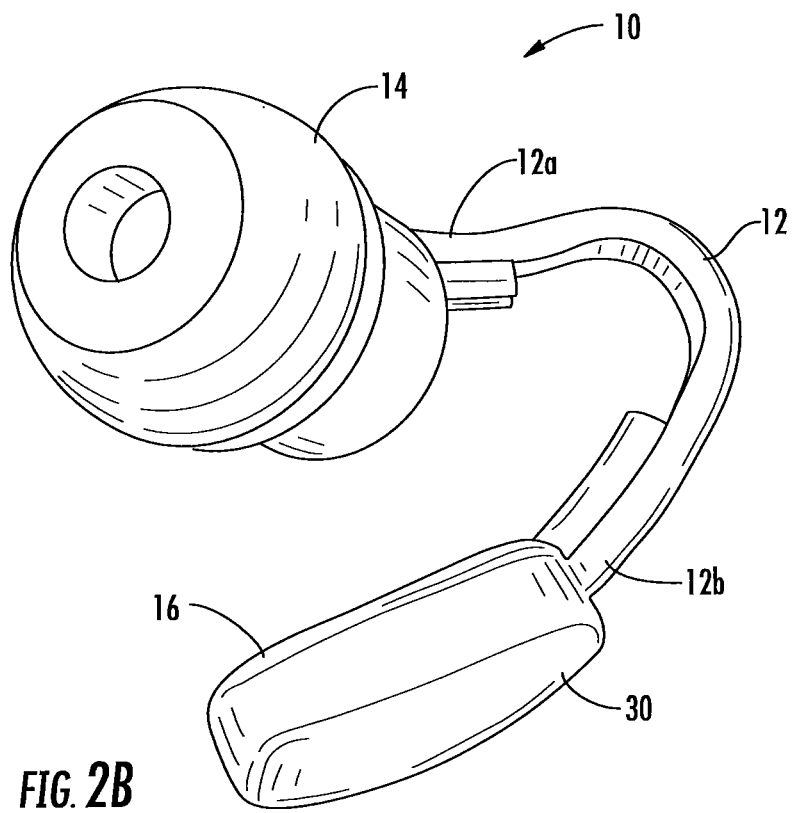
Figure 2C:
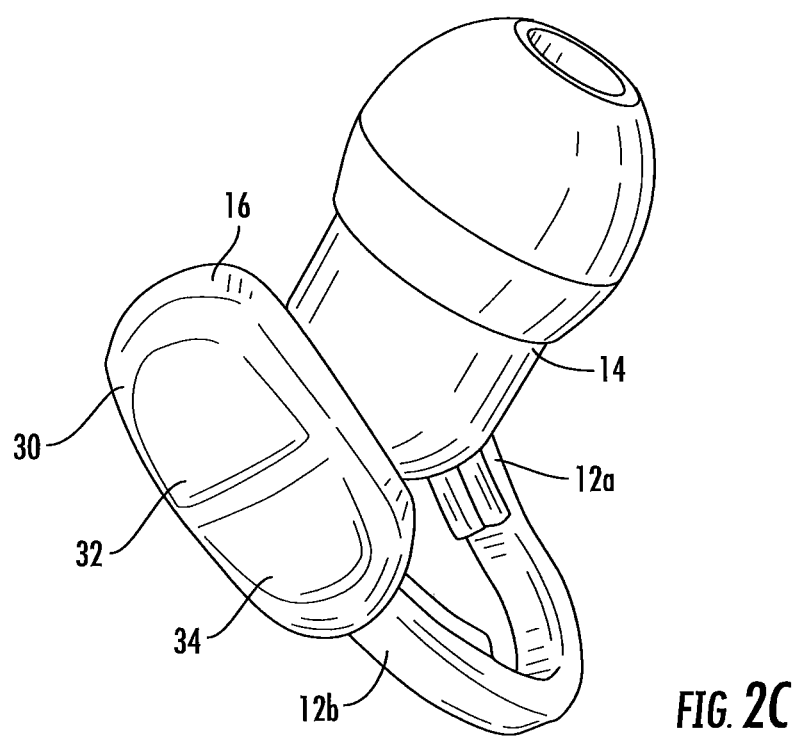

Referring to FIGS. 2A-2C, a monitoring device 10 according to some embodiments of the present invention is illustrated. The illustrated monitoring device 10 includes a biasing element 12 having opposite first and second end portions 12a, 12b. An earbud 14 is attached to the biasing element first end portion 12a, and a sensing element 16 is attached to the biasing element second end portion 12b. The sensing element 16 may comprise sensor components and may preferably be smaller in mass than the mass of the earbud 14, and may be substantially less. For example, in some embodiments, the earbud mass may be at least 10% greater than the sensing element mass, may be at least 20% greater than the sensing element mass, may be at least 30% greater than the sensing element mass, may be at least 40% greater than the sensing element mass, may be at least 50% greater than the sensing element mass, may be at least 60% greater than the sensing element mass, may be at least 70% greater than the sensing element mass, may be at least 80% greater than the sensing element mass, may be at least 90% greater than the sensing element mass, may be at least 100% greater than the sensing element mass, may be 200% or more than the sensing element mass, etc. Although embodiments of the present invention may function sufficiently well with the earbud 14 having a smaller mass than that of the sensor element 16, in general, the mass of the earbud is preferably larger than that of the sensor element by a sufficient degree so that the earbud serves as the primary frame of reference (the mechanical support reference) for the monitoring device.

Substantial motion decoupling can be achieved by the sensing element 16 having a mass that is smaller than the mass of the earbud 14. For example, if the monitoring device 10 weighs ten (10) grams and the earbud 14 has a mass of nine (9) grams and the sensor element has a mass of one (1) gram, the momentum caused by the monitoring device 10 accelerating may be substantially less on the sensing element 16 such that the sensing element 16 experiences less distance travelled. Sensor noise is reduced by stopping the monitoring device 10 momentum from causing the sensing element 16 to move as far. Sensor jitter from movement is the largest controllable contributor to a noisy signal. The more one can decouple device mass from sensor mass the cleaner the signal gets. The more the sensing element 16 mass is reduced and the lower the spring constant, the less sensor movement is experienced from the monitoring device 10 mass accelerating on each footstep of the subject, for example.

Figure 4:
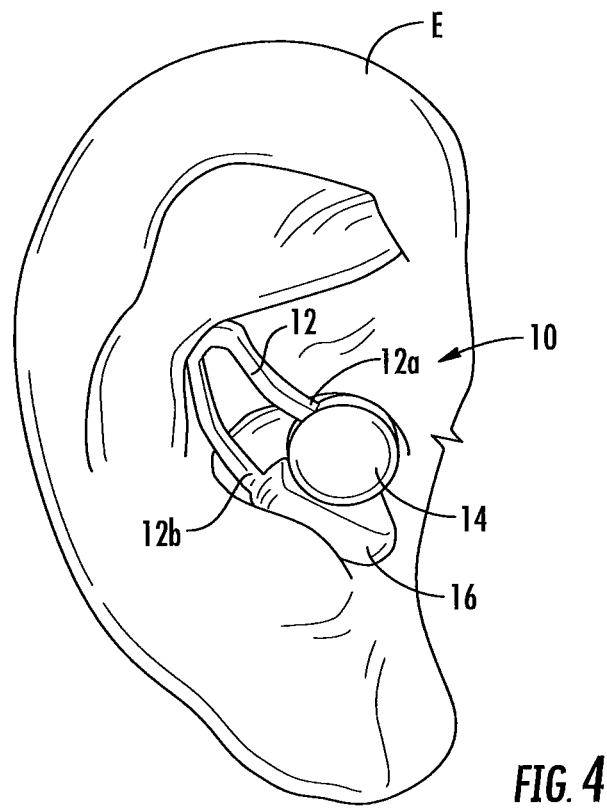
FIG. 4 illustrates the monitoring device of FIGS. 2A-2C secured within the ear of a person.

The monitoring device 10 is configured to be attached to an ear of a subject such that the earbud 14 is secured within the ear and the biasing element 12 urges the sensing element 16 into contact with the ear at a particular location, for example, as illustrated in FIG. 4. In addition, the biasing element 12 decouples motion of the larger mass earbud 14 from the smaller mass sensing element 16. As such, the motion of sensing element 16 is more closely tied to the motion of the subject and less tied to the motion of the earbud, for example when the subject is exercising or undergoing other motion. For example, the motion between the sensing element 16 and the subject may be less than the motion between the sensing element 16 and the earbud 14.

The earbud 14 may have various shapes and configurations and is not limited to the illustrated shape. The sensing element 16 may have various shapes and configurations and is not limited to the illustrated shape. In addition, a wire (not shown) may connect an audio device to the earbud, as would be understood by those of skill in the art. Moreover, the earbud 14 may comprise a speaker, and/or the monitoring device 10 may generally comprise a speaker and microphone. Various types of speakers or microphones may be used. In some cases a bone conduction microphone or speaker may be used. In some embodiments, a speaker may intentionally not be present and an opening or hole may exist in the earbud to expose the ear canal to the outside world. Such an embodiment may be useful for the case where biometric/physiological monitoring is desired without the user's ear canal being blocked-off from ambient sounds. FIG. 4 illustrates the monitoring device 10 of FIGS. 2A-2C secured within the ear of a person.

Figure 3:
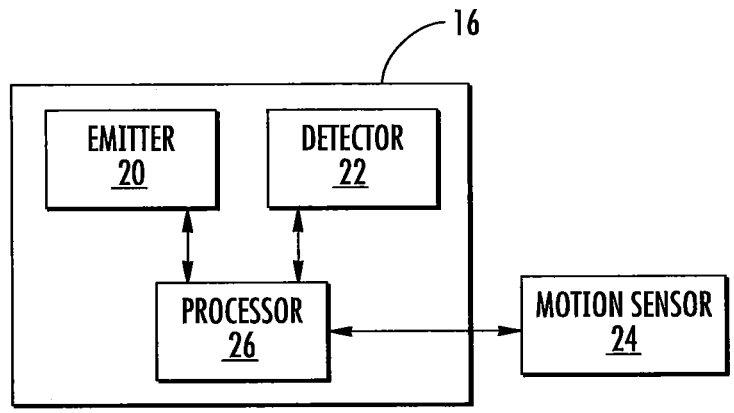
FIG. 3 schematically illustrates a sensing element utilized in monitoring devices, according to some embodiments of the present invention.

In some embodiments of the present invention, the sensing element 16 includes at least one energy emitter 20 (FIG. 3) configured to direct energy at a target region of the ear (or for other embodiments of the present invention, at a target region of another portion of the body of a subject, such as an appendage) and at least one detector 22 (FIG. 3) configured to detect an energy response signal from the target region and/or a region adjacent the target region. For example, the at least one energy emitter 20 is configured to direct electromagnetic radiation, mechanical energy, acoustical energy, electrical energy, and/or thermal energy at the target region, and the at least one detector 22 is configured to detect electromagnetic radiation, mechanical energy, acoustical energy, electrical energy, and/or thermal energy. In some embodiments, the at least one energy emitter comprises at least one optical emitter and the at least one detector comprises at least one optical detector. Exemplary optical detectors include, but are not limited to photodiodes, photodetectors, phototransistors, thyristors, solid state devices, optical chipsets, whether analog or digital, or the like. Many types of compact optical detectors exist in the marketplace today and comprise various'well-known methods of generating analog or digital outputs. Exemplary optical emitters include, but are not limited to light-emitting diodes (LEDs), laser diodes (LDs), compact incandescent bulbs, micro-plasma emitters, IR blackbody sources, or the like.

Some emitters, detectors, or emitter-detector modules may also comprise one or more processors 26 for signal conditioning, ND conversion, voltage-to-frequency conversion, level translation, and general signal processing of signals from the detector. Additionally, one or more processors 26 may be used to control the powering (electrical biasing) of the emitters and/or detectors. A few examples are provided in U.S. Patent Application Publication No. 2012/0197093, which is incorporated herein by reference in its entirety. In some embodiments, the processor 26 may not be located within the sensing element 16 itself and may even be located outside of the monitoring device 10 altogether, as long as the processor 26 is in electrical communication with the sensing element 16. Moreover, processor 26 may represent multiple processors distributed within the monitoring device 10 and/or outside of the monitoring device 10.

The energy may be pulsed energy generated by an energy emitter 20. For example, a pulsed driving circuit (not shown) may be used to drive at least one energy emitter 20 at one or more pulsed frequencies to interrogate a target region with pulsed energy. An energy response caused by this interaction is detected by at least one detector 22, which is configured to detect energy in the forms described above, but typically in the form of scattered optical energy. A motion/position sensor 24 (e.g., an inertial sensor, MEMS (micro-electro-mechanical systems) sensor, accelerometer, gyroscope, capacitive sensor, inductive sensor, acoustic sensor, optical sensor, piezoelectric sensor, etc.) may be configured to measure movement, positional changes, or inertial changes in the vicinity of the target region, such as gross body motion, skin motion, or the like. The motion/position sensor 24 may be located within the sensing element. In other embodiments, the biasing element 12 may include a motion/position sensor 24 that is configured to detect motion of the biasing element 12 and/or sensing element 16, or the relative motion between the earbud 14 and sensing element 16.

The motion/position sensor 24 may also serve as a noise reference by a neighboring or remote processor (such as processor 26) for attenuating or removing motion noise from physiological signals picked up by the detector 22. Noise attenuation and removal is described in detail in U.S. Pat. Nos. 8,157,730, 8,251,903, U.S. Patent Application Publication No. 2008/0146890, U.S. Patent Application Publication No. 2010/0217098, U.S. Patent Application Publication No. 2010/0217102, U.S. Provisional Patent Application No. 61/750,490, PCT Application No. US2012/071593, PCT Application No. US2012/071594, and PCT Application No. US2012/048079, which are incorporated herein by reference in their entireties.

In some embodiments, the monitoring device 10 includes a signal processor 26 (FIG. 3) that is configured to receive and process signals produced by the at least one detector 16. The monitoring device 10 may include other components such as one or more analog-to-digital convertors (not shown) for the output of the at least one detector 22, one or more filters such as optical filters (snot shown) for removing the effects of time-varying environmental interference, one or more analog and/or digital filters for removing motion artifacts in an energy response signal, passive electronic components, etc., as would be understood by one skilled in the art. The monitoring device 10 may include various other devices, such as other types of physiological sensors and environmental sensors (not shown). The monitoring device 10 may also include at least one wireless module (not shown) for communicating with a remote device, and/or at least one memory storage device (not shown). An exemplary wireless module may include a wireless chip, antenna, or RFID tag. In some embodiments, the wireless module may include a low-range wireless chip or chipset, such as a Bluetooth®, ANT+, and/or ZigBee chip. A battery (not shown), such as a lithium polymer battery or other portable battery, may be included within the monitoring device 10 and may be charged via a USB charge port, for example.

In the illustrated embodiment of FIGS. 2A-2C, the sensing element 16 includes a surface 30 that engages a portion of the ear E of a subject. In some embodiments, at least part of the surface 30 may be contoured to conform to a shape of a portion of the ear of a subject. Also, in the illustrated embodiment of FIGS. 2A-2C, one or more energy emitters 20 and detectors 22 are located within the sensing element 16. A pair of windows 32, 34 are included in the illustrated sensing element surface 30 through which energy passes from the one or more energy emitters 22, and through which energy is collected by the one or more detectors 22. Each window 32, 34 is formed from a material that allows energy to pass therethrough. For example, if an optical emitter and detector are utilized, the windows 32, 34 are formed from material that allows light to pass therethrough. In some embodiments, the windows 32, 34 may include one or more openings. In some embodiments, a single window is utilized instead of a pair of windows.

Although the windows 32, 34 illustrated in FIG. 2C may be shown as flush with the overall sensor surface 30, it should be noted that the windows 32, 34 at the sensor surface 30 may be recessed with respect to the sensor surface 30 and may not come into physical contact with the skin of the ear of a user of the monitoring device 10. A flush, protruding, or recessed window(s) (32, 34) may be acceptable. Furthermore, the window(s) (32, 34) in some embodiments may comprise air such that the excitation energy entering or leaving the sensor element 16 may pass through air.

In some embodiments of the present invention, one or both of the windows 32, 34 may be in optical communication with an optical lens (not shown). The lens may be configured to focus light emitted by an optical emitter onto one or more portions of an ear and/or to focus collected light on a detector. Various types of lens geometries may be employed, such as concave, convex, collimating, and the like. Light guides (such as light pipes, fiber optics, or the like) may also be incorporated for this stated purpose. Exemplary light guides and sensing element geometries that may be utilized in accordance with some embodiments of the present invention are described, for example, in U.S. Patent Application Publication No. 2010/0217102, U.S. Patent Application Publication No. 2013/0131519, and U.S. Patent Application Publication No. 2010/0217098, which are incorporated herein by reference in their entireties.

As will be described below, in other embodiments of the present invention, an optical energy emitter 20 and/or optical detector 22 may be located within the monitoring device 10, in the earbud 14 or sensing element 16. One or more light guides are utilized to deliver light from the optical emitter into an ear region of the subject via the light guide distal end, and/or to collect light from an ear region of the subject via the light guide distal end and deliver collected light to the optical detector.

Figure 5A:
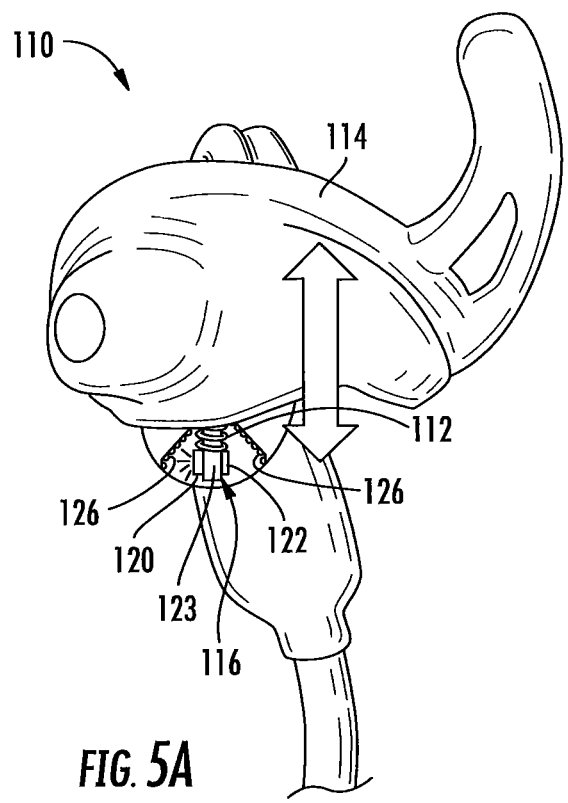
FIG. 5A is a perspective view of a monitoring device for attachment to an ear of a person, according to some embodiments of the present invention, and wherein a sensor module is movably secured to the housing of the monitoring device to decouple motion of the housing from the sensor module.
Figure 5B:
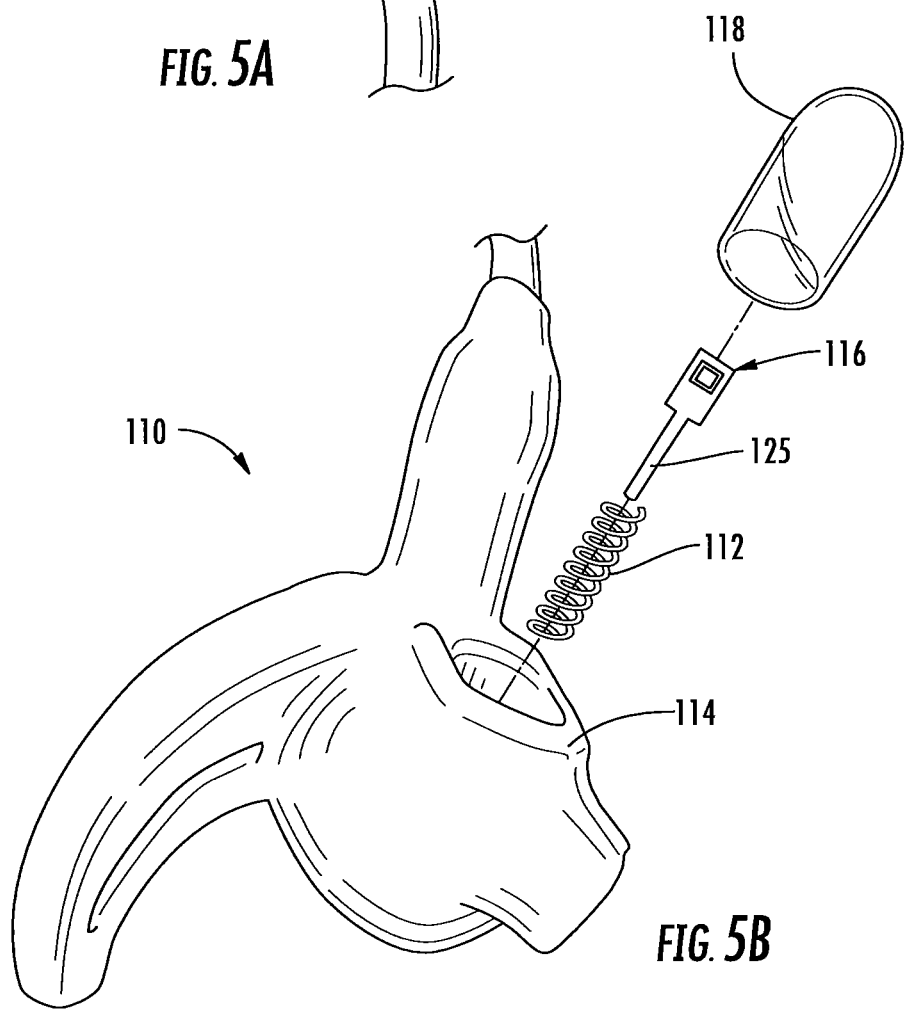
FIG. 5B is an exploded, perspective view of the monitoring device of FIG. 5A.

FIGS. 5A and 5B illustrate a monitoring device 110, according to other embodiments of the present invention. The monitoring device 110 includes a housing 114 configured to be attached to an ear of a subject, and a sensing element 116 movably secured to the housing 114 via a biasing element 112 (e.g., a coil spring, or other substantially compressible structure or material, etc.). In some embodiments, the biasing element 112 may include a motion sensor (not shown) that is configured to detect motion of the biasing element 112 and/or sensing element 116.

Though non-limiting, the biasing element 112 may have a spring constant between about 0.1 N/m and about 200 N/m. If a resilient material is utilized as the biasing element 112, the resilient material may have a durometer range from about 10 (Type OO—ASTM D2240) to 80 (Type A—ASTM D2240), and a hardness range of about 20-50 Shore A. Exemplary springs that may be utilized as the biasing element 112 can be molded from acetal, polyester, polyetherimide, or another suitable polymer, or could be formed from metal, such as steel. Exemplary spring manufacturers include, but are not limited to, Lee Spring (Greensboro, N.C.) and Century Spring Corp. (Los Angeles, Calif.). An exemplary resilient material that may be used as a biasing element includes, but is not limited to, silicone (Dow Corning Corp., Midland, Mich.). However, various other materials may be used, such as stretchy neoprene (polyurethane).

The illustrated sensing element 116 includes a printed circuit board (PCB) 123 with an optical emitter 120 and an optical detector 122 attached thereto. The PCB 123 also includes an elongated guide rod 125 that is inserted within the illustrated biasing element 112. It should be noted that while the direction of light emission in FIG. 5A is shown radiating outwards in one embodiment, the preferred direction of emission light is the region between the anti-tragus and concha of the ear as described, for example, in U.S. Patent Application Publication No. 2010/0217098, U.S. Patent Application Publication No. 2010/0217102, and also in U.S. Patent Application Publication No. 2013/0131519 which is incorporated herein by reference in its entirety. In the particular embodiment shown in FIG. 5A, optically reflective walls 126 are positioned to direct light towards the region between the anti-tragus and concha of the ear.

The monitoring device 110 also includes a cover 118 for the sensing element 116. The cover 118 may be transmissive to energy (e.g., electromagnetic radiation, acoustical energy, electrical energy, and/or thermal energy, etc.) emitted by an emitter associated with the sensing element 116 and energy detected by a detector associated with the sensing element 116. For example, if the sensing element 116 includes an optical emitter and detector, the cover 118 may be transmissive to optical wavelengths of the optical emitter and detector. In the illustrated embodiment, the cover 118 may also include reflective surfaces or walls 126 to facilitate directing energy from the emitter 120 toward the ear of a user and directing energy from the ear to the detector 122. The angle of the reflective wall(s) 126 with respect to the axis of the elongated rod 125 is shown at approximately forty-five degrees (45°) in FIG. 5A, but this should not be considered limiting. The angle of the reflective walls 126 will depend primarily on the direction of the emission/detection face of the optical emitter/detector with respect to the region between the anti-tragus and concha of the ear. For example, if the emitter 120 and detector 122 are directed with their respective emission/detection faces located in the direction of the anti-tragus, the angle of the reflective surface(s) 126 may be ninety degrees)(90° with respect to the axis of the elongated rod 125.

The illustrated cover 118 is attached to the sensing element 116 and moves with the sensing element. The cover 118 can be attached to the sensing element 116 in various ways. For example, in some embodiments, the cover 118 may be overmolded onto the sensing element 116 such that the cover at least partially conforms to the shape of the sensing element 116 components. In other embodiments, the cover 118 may be attached with a suitable transmissive adhesive. Exemplary adhesive materials include, but are not limited to, glue, tape, resin, gel, filler material, molded material, etc. In some embodiments, the cover 118 is attached to the sensing element 116 via heatstaking, one or more mechanical fasteners, or other suitable methods. In some embodiments, the sensing element 116 and cover 118 may comprise an integrated unit (via overmold and/or adhesive) that can be connected to the rod 123 or spring 112.

It should be noted that in some embodiments, an optical filter may be placed over the emitter 120 or detector 122 in one or more ways, for example, as described in U.S. Patent Application Publication No. 2010/0217098, U.S. Patent Application Publication No. 2010/0217102, U.S. Patent Application Publication No. 2013/0131519, and U.S. Patent Application Publication No. 2012/0197093. Additionally, the cover 118 may comprise an optical filter or optical dye focused on the wavelength of interest, which is chiefly determined by the choice of the optical emitter 120. As an example, if 940 nm wavelength light is desired for emission by the optical emitter, in order to help overcome external (e.g., sunlight, etc.) noise pollution on the optical detector 122 (e.g., as described in U.S. Patent Application Publication No. 2012/0197093), then the optical filter may be tuned to the infrared range centered around 940 nm. As a specific example of this, one may use GENTEX-E800 dye dispersed in a polycarbonate or acrylic cover 118.

In the illustrated embodiment, the housing 114 of the monitoring device 110 has a much larger mass than the sensing element 116 and cover 118, and the biasing element 112 decouples motion of the housing 114 from the sensing element 116 and cover 118.

In some embodiments, the monitoring device 110 includes a signal processor 26 (FIG. 3) that is configured to receive and process signals produced by the optical detector 122. The monitoring device 110 may include other components such as one or more analog-to-digital convertors (not shown) for the output of the optical detector 122, one or more filters such as optical filters (not shown) for removing the effects of time-varying environmental interference, one or more analog and/or digital filters for removing motion artifacts in an energy response signal, passive electronic components, etc., as would be understood by one skilled in the art. The monitoring device 110 may include various other devices, such as other types of physiological sensors and environmental sensors (not shown). The monitoring device 110 may also include at least one wireless module (not shown) for communicating with a remote device, and/or at least one memory storage device (not shown). An exemplary wireless module may include a wireless chip, antenna, or RFID tag. In some embodiments, the wireless module may include a low-range wireless chip or chipset, such as a Bluetooth®, ANT+, and/or ZigBee chip. A battery (not shown), such as a lithium polymer battery or other portable battery, may be included within the monitoring device 110 and may be charged via a USB charge port, for example.

FIGS. 18A-18B and 19A-19B illustrate a monitoring device 710 configured to be attached to an ear of a subject, according to other embodiments of the present invention. The monitoring device 710 includes a housing 714, a core element 718, and a sensing element 716. A sound port 720 is formed in the core element and is in acoustic communication with a speaker (not shown) within the housing 714. The sensing element 716 may include all of the functionality of the sensing device 16 described above. For example, the sensing element 716 may include at least one energy emitter 20 (FIG. 3) configured to direct energy at a target region of the ear and at least one detector 22 (FIG. 3) configured to detect an energy response signal from the target region or a region adjacent the target region, as described above, to sense physiological signals from the body of the subject.

A cover 818 formed from compressible/resilient material, such as a gel material, etc., surrounds the core element 718, as illustrated in FIGS. 19A-19B. The cover 818 at least partially surrounds the sensing element 716, and serves as a biasing element that decouples motion of the housing 714 and core element 718 from the sensing element 716. The illustrated cover 818 has a sound port 820 formed therethrough that is in acoustic communication with sound port 720.

Also, as illustrated in FIGS. 19A-19B, the monitoring device 710 includes an arcuate resilient member 822 that is configured to stabilize the monitoring device 710 within the ear of a subject, as would be understood by one skilled in the art. Numerous types of stabilizers (also referred to as covers, tips, or housings) that may be utilized as member 822 are well known in the art, (e.g., see U.S. Patent Application Publication No. 2010/0217098, U.S. Patent Application Publication No. 2010/0217102, and U.S. Patent Application Publication No. 2012/0197093) each finding various points of reference for holding an earbud within the ear.

The illustrated monitoring device 710 also includes an additional flexible member 824 formed from a compressible/resilient material, such as a gel material, etc. This flexible member 824 is attached to the cover 818 and extends below the plane of the sensing element 816, such that the sensing element 816 is recessed within the flexible member 824. The flexible member 824 effectively extends the cover 818 so that it can compress in the region including, and in between, the anti-tragus and crus helix of a subject's ear. A barrier between the emitter and detector may also be preserved as the flexible member 824 extends to prevent optical crosstalk between the emitter and detector of the sensing element 716.

The flexible member 824 serves as a biasing element that decouples motion of the housing 714 and core element 718 from the sensing element 716. As such, the illustrated monitoring device 710 effectively includes two biasing elements that facilitate the decoupling of motion of the housing 714 and core element 718 from the sensing element 716: flexible cover 818 and flexible member 824.

In some embodiments, the monitoring device 710 includes a signal processor 26 (FIG. 3) that is configured to receive and process signals produced by the at least one detector 22. The monitoring device 710 may include other components such as one or more analog-to-digital convertors (not shown) for the output of the at least one detector 22, one or more filters such as optical filters (not shown) for removing the effects of time-varying environmental interference, one or more analog and/or digital filters for removing motion artifacts in an energy response signal, passive electronic components, etc., as would be understood by one skilled in the art. The monitoring device 710 may include various other devices, such as other types of physiological sensors and environmental sensors (not shown). The monitoring device 710 may also include at least one wireless module (not shown) for communicating with a remote device, and/or at least one memory storage device (not shown). An exemplary wireless module may include a wireless chip, antenna, or RFID tag. In some embodiments, the wireless module may include a low-range wireless chip or chipset, such as a Bluetooth®, ANT+, and/or ZigBee chip. A battery (not shown), such as a lithium polymer battery or other portable battery, may be included within the monitoring device 710 and may be charged via a USB charge port, for example.

Figure 6:
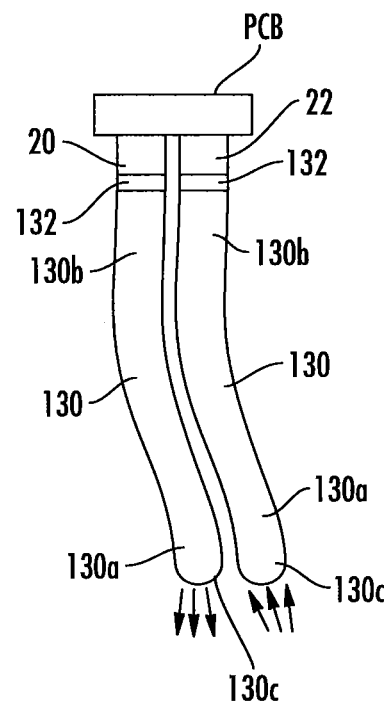
FIG. 6 illustrates elongated light guides that may be utilized with monitoring devices, according to some embodiments of the present invention, such that an optical emitter and optical detector can be located remotely from a sensing element of a monitoring device.
Figure 7:
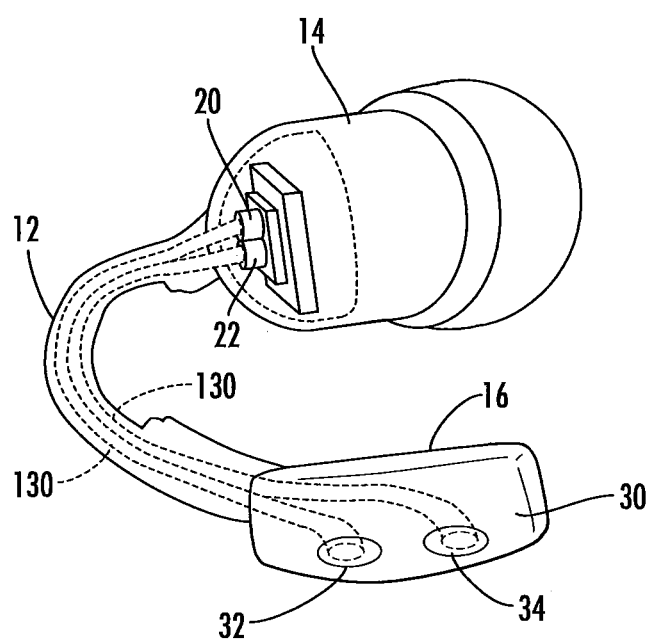
FIG. 7 illustrates the monitoring device of FIGS. 2A-2C with an optical emitter and detector located within the earbud and with elongated light guides extending from the optical emitter and detector to the sensing element, according to some embodiments of the present invention.

In some embodiments of the present invention, as illustrated in FIGS. 2A-2C, an optical emitter 20 and optical detector 22 are attached to or disposed within the sensing element 16. However, in other embodiments of the present invention, an optical emitter 20 and/or optical detector 22 can be located remotely from the sensing element 16. For example, as illustrated in FIG. 7, an optical emitter 20 and optical detector 22 may be located within the earbud 14. A pair of elongated light guides 130, such as illustrated in FIG. 6, are in optical communication with the optical emitter 20 and optical detector 22 via proximal end portions 130b and extend from the optical emitter 20 and optical detector 22 at least partially through the biasing element 12 to the sensing element 16. The sensing element 16 includes a pair of windows 32, 34 in the surface 30 thereof. Each light guide distal end 130a is positioned adjacent a respective window 32, 34, as illustrated. As such, the light guide 130 in optical communication with the optical emitter 20 can deliver light from the optical emitter 20 into an ear region of the subject, and the light guide 130 in optical communication with the optical detector 22 can collect light from the ear region of the subject and deliver collected light to the optical detector 22.

The distance between the sensing element windows 32 and 34 is long enough to reduce optical backscatter noise and close enough to emit and detect light from a target region and/or a region adjacent the target region. Distances on the order of millimeters have been found to be ideal in practice. Moreover, the material between windows 32, 34 is sufficiently optically opaque to reduce cross-talk between the emitter 20 and detector 22.

Each light guide 130 may be formed from various types of light transmissive material, typically with a refractive index greater than about 1.1. In some embodiments, a light guide 130 may be formed from an elastomeric light transmissive material. Exemplary light guide materials include, but are not limited to, polycarbonate, acrylic, silicone, and polyurethane. In some embodiments, a light guide 130 may be surrounded or partially surrounded by a cladding material that is configured to block light from an external source, such as room light, sunlight, etc., from entering the light guide 130. The distal free end surface 130c of each light guide 130 may have a variety of shapes and/or configurations, more than exemplarily shown in FIG. 6. Various types and configurations of light guides may be utilized, for example, as described in U.S. Patent Application Publication No. 2010/0217102 and U.S. Patent Application Publication No. 2013/0131519.

As illustrated in FIG. 6, optical coupling material 132 may be applied to one or both of the optical emitter 20 and optical detector 22. A light guide 130 is in optical communication with the optical emitter 20 and optical detector 22 via the optical coupling material 132. The optical coupling material 132 may comprise a material that effectively couples light from the optical emitter 20 to the light guide 130 or from the light guide 130 to the optical detector 22. Examples of suitable materials include, but are not limited to, glue, epoxy, tape, resin, gel, oil, filler material, molded material (such as a plastic, acrylic, and/or polycarbonate) or the like.

In some embodiments of the present invention, the sensing element 16 may have one or more windows 32, 34 in the surface 30 thereof and the distal free end surface 130c of one or both of the light guides 130 may extend to the windows 32, 34. In other embodiments, one or both of the windows 32, 34 may be apertures formed through the surface 30 and the distal free end surface 130c of one or both of the light guides 130 may extend to or through the apertures.

Figure 9:
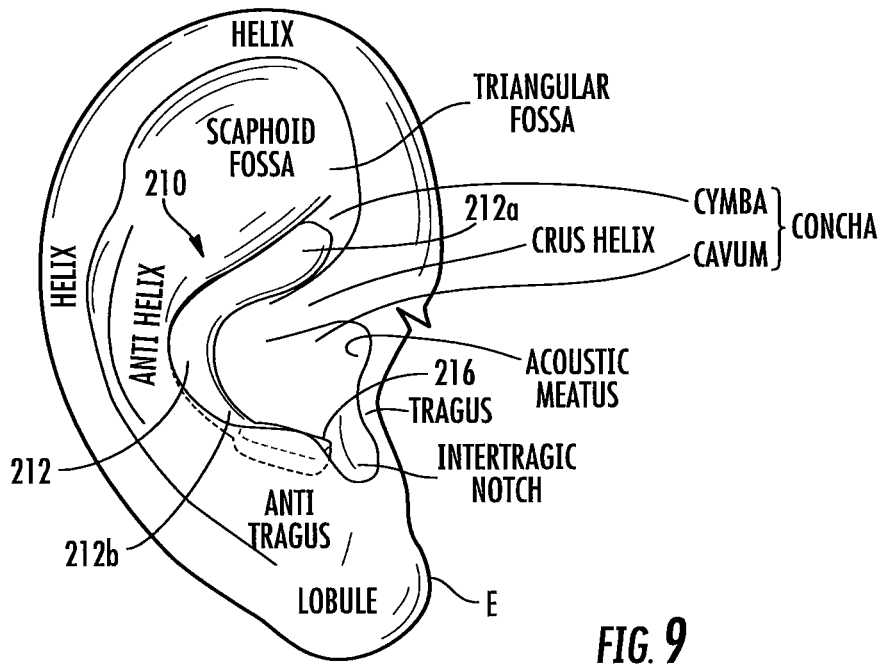
FIG. 9 illustrates a human ear with various portions thereof labeled and with the monitoring device of FIG. 10 secured therewithin.
Figure 10:
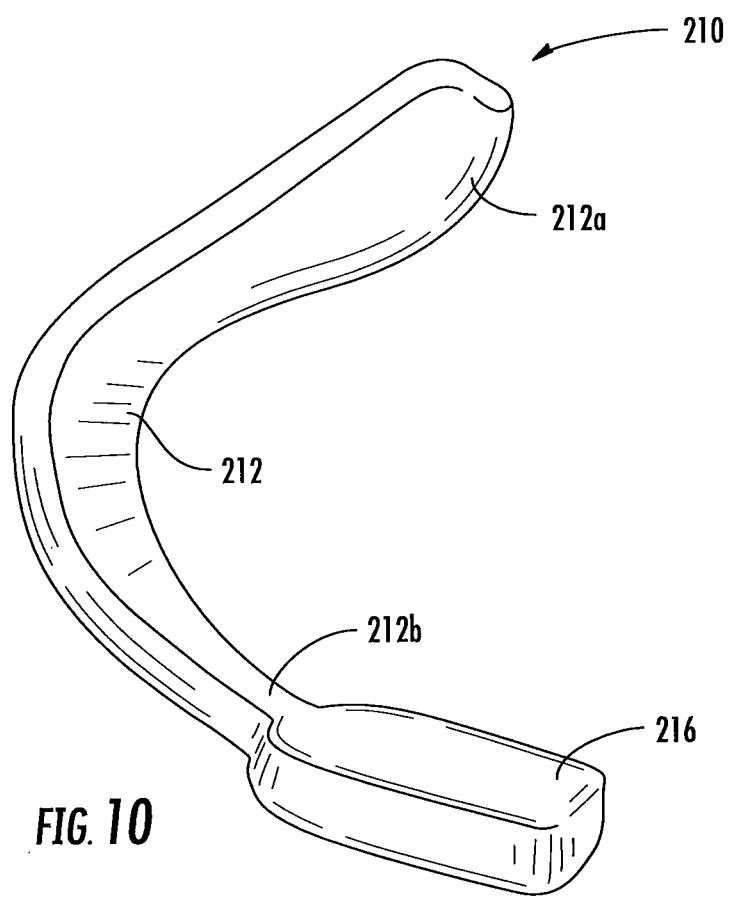
FIG. 10 is a perspective view of a monitoring device having a sensor module configured to be attached to an ear of a person via a biasing member, according to some embodiments of the present invention, and wherein the biasing member is configured to decouple motion of the ear from the sensor module.

Referring now to FIG. 10, a monitoring device 210, according to other embodiments of the present invention, is illustrated. The illustrated monitoring device 210 includes a biasing element 212 having opposite first and second end portions 212a, 212b. A sensing element 216 is attached to the biasing element second end portion 212b. The monitoring device 210 is configured to be attached to an ear E of a subject such that the biasing element first end portion 212a engages the ear at a first location and such that the sensing element is urged by the biasing member into contact with the ear at a second location, as illustrated in FIG. 9. The sensing element 216 may include all of the functionality of the sensing device 16 described above with respect to FIGS. 2A-2C, and may have the same overall structure as that of sensing device 16. For example, the sensing element 216 may include at least one energy emitter 20 (FIG. 3) configured to direct energy at a target region of the ear and at least one detector 22 (FIG. 3) configured to detect an energy response signal from the target region or a region adjacent the target region, as described above, to sense physiological signals from the body of the subject.

In some embodiments, the monitoring device 210 includes a signal processor 26 (FIG. 3) that is configured to receive and process signals produced by the at least one detector 22. The monitoring device 210 may include other components such as one or more analog-to-digital convertors (not shown) for the output of the at least one detector 22, one or more filters such as optical filters (not shown) for removing the effects of time-varying environmental interference, one or more analog and/or digital filters for removing motion artifacts in an energy response signal, passive electronic components, etc., as would be understood by one skilled in the art. The monitoring device 210 may include various other devices, such as other types of physiological sensors and environmental sensors (not shown). The monitoring device 210 may also include at least one wireless module (not shown) for communicating with a remote device, and/or at least one memory storage device (not shown). An exemplary wireless module may include a wireless chip, antenna, or RFID tag. In some embodiments, the wireless module may include a low-range wireless chip or chipset, such as a Bluetooth®, ANT+, and/or ZigBee chip. A battery (not shown), such as a lithium polymer battery or other portable battery, may be included within the monitoring device 210 and may be charged via a USB charge port, for example.

The illustrated embodiment of FIG. 10 does not utilize an earbud portion (e.g., 14, FIGS. 2A-2C) or a stabilization member (314, FIG. 11) for support within the ear. The first end portion 212a of the monitoring device 210 illustrated in FIG. 10 may be supported within the ear primarily by the ear region including, and in between, the anti-helix and crus helix, as shown in FIG. 9. Alternatively, the first end portion 212a may be supported primarily by the ear region including, and in between, the crus helix and acoustic meatus. More generally, the first end portion 212a and second end portion 212b may be supported by geometrically opposing ear features.

The monitoring device 210 may be oriented within a subject's ear in various ways. For example, the sensing element 216 location may be "flipped". Referring to FIG. 9, the second end portion 212b may be supported by the ear region including, and in between, the anti-helix and crus helix, and the first end portion 212a may be supported by the ear region including, and in between, the crus helix and anti-tragus. In this "flipped" orientation, the sensing element 216 may rest against the anti-helix of the ear rather than the anti-tragus. Though the anti-helix may have substantially less blood flow than that of the anti-tragus, it may present less motion artifacts for some user activities, and so this configuration may be useful for some physiological monitoring applications.

Figure 11:
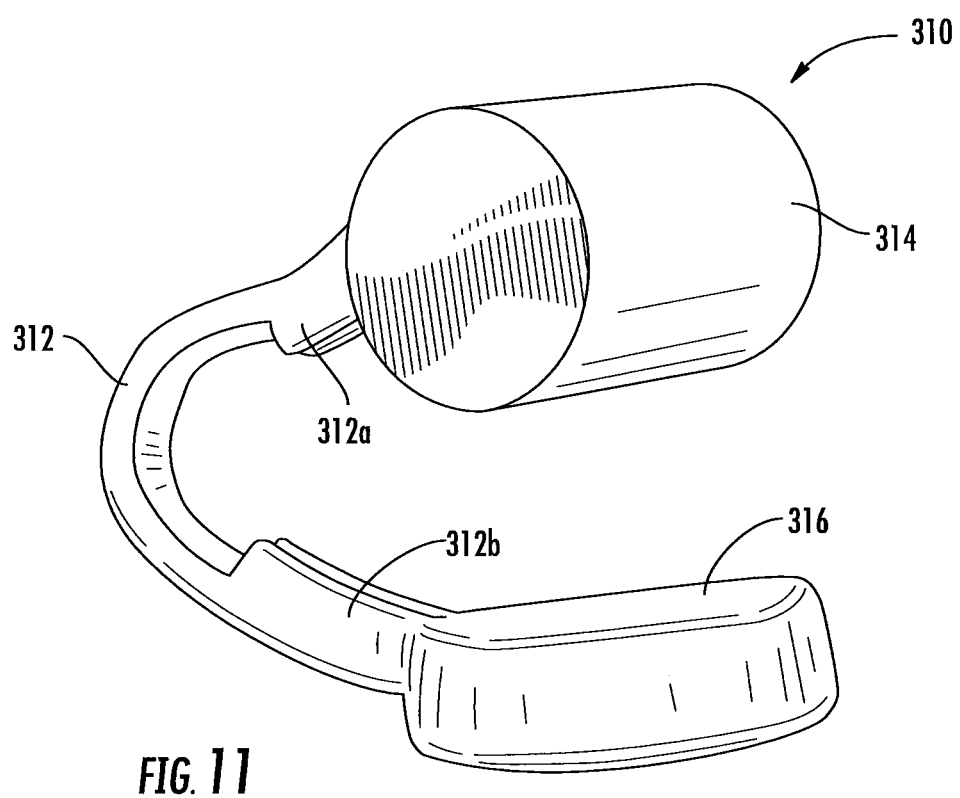
FIG. 11 is a perspective view of a monitoring device having a stabilizing member configured to be inserted within an ear of a person and a sensor module attached to the stabilizing member via a biasing member, according to some embodiments of the present invention, and wherein the biasing member is configured to decouple motion of the stabilizing member from the sensor module.

Referring now to FIG. 11, a monitoring device 310, according to other embodiments of the present invention, is illustrated. The illustrated monitoring device 310 includes a biasing element 312 having opposite first and second end portions 312a, 312b. A stabilization member 314 that is configured to be at least partially inserted into the ear or ear canal is attached to the biasing element first end portion 312a. In this embodiment, the stabilization member 314 may not contain a speaker and may not serve the function of an audio earbud. In some embodiments of this configuration, because a speaker is not required, the stabilization member 314 may have a hole completely through one or more axes to allow sound to freely pass from the environment to the eardrum of the subject wearing the monitoring device 310. The stabilization member 314 facilitates attachment of the monitoring device 310 to an ear of a subject.

The monitoring devices 210 and 310 may be particularly useful for subjects who want to monitor their vital signs but do not want to listen to music or do not want to have their ear canal blocked-off from sound. Additionally, if constructed with waterproof housing, the monitoring devices 210 and 310 may be especially suited for swimmers who may not want to hear sound from speakers during physiological monitoring.

Figure 8:
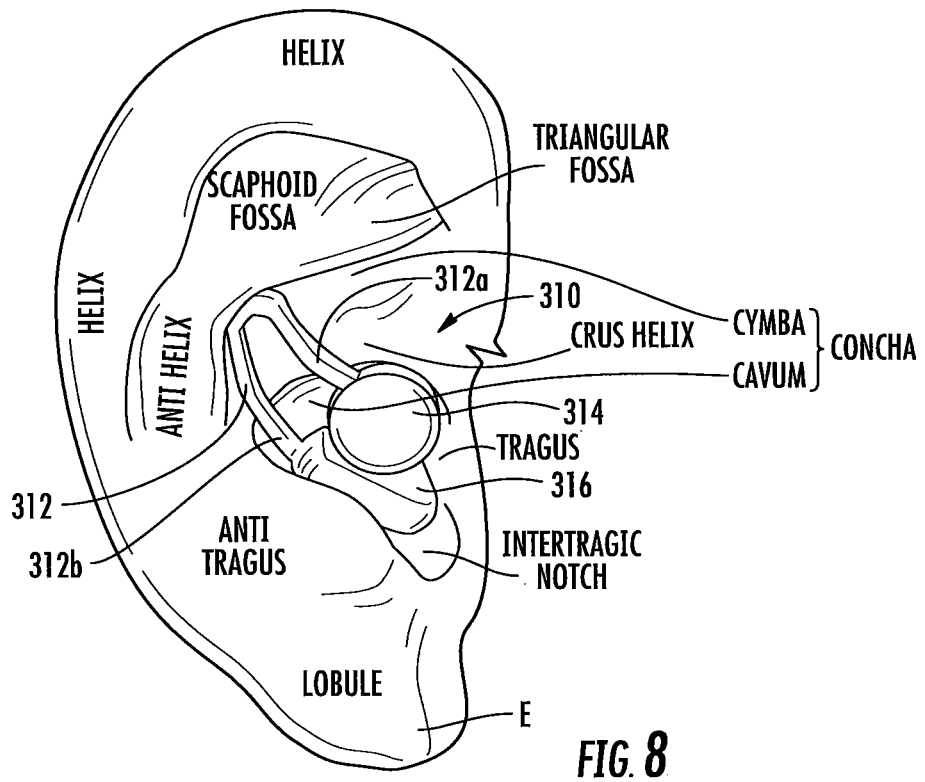
FIG. 8 illustrates a human ear with various portions thereof labeled and with the monitoring device of FIG. 11 secured therewithin.

A sensing element 316 is attached to the biasing element second end portion 312b. The monitoring device 310 is configured to be attached to an ear E of a subject such that the sensing element 316 is urged by the biasing member 312 into contact with the ear, as illustrated in FIG. 8. The sensing element 316 may include all of the functionality of the sensing device 16 described above. For example, the sensing element 316 may include at least one energy emitter 20 (FIG. 3) configured to direct energy at a target region of the ear and at least one detector 22 (FIG. 3) configured to detect an energy response signal from the target region or a region adjacent the target region, as described above, to sense physiological signals from the body of the subject. With the illustrated configuration of the monitoring device 310, the sensing element 316 may be preferably biased to direct and/or detect energy from the region of the ear between the anti-tragus and concha of the ear, as this region has been found to provide a sufficiently high blood flow signal intensity while also being resilient to motion artifacts.

In some embodiments, the monitoring device 310 includes a signal processor 26 (FIG. 3) that is configured to receive and process signals produced by the at least one detector 22. The monitoring device 310 may include other components such as one or more analog-to-digital convertors (not shown) for the output of the at least one detector 22, one or more filters such as optical filters (not shown) for removing the effects of time-varying environmental interference, one or more analog and/or digital filters for removing motion artifacts in an energy response signal, passive electronic components, etc., as would be understood by one skilled in the art. The monitoring device 310 may include various other devices, such as other types of physiological sensors and environmental sensors (not shown). The monitoring device 310 may also include at least one wireless module (not shown) for communicating with a remote device, and/or at least one memory storage device (not shown). An exemplary wireless module may include a wireless chip, antenna, or RFID tag. In some embodiments, the wireless module may include a low-range wireless chip or chipset, such as a Bluetooth®, ANT+, and/or ZigBee chip. A battery (not shown), such as a lithium polymer battery or other portable battery, may be included within the monitoring device 310 and may be charged via a USB charge port, for example.

The small size of the monitoring devices 210 and 310 may preclude space for signal processing electronics (26) and battery power. For this reason, these monitoring devices may also be attached/wired to additional structures that house necessary electronics and/or battery power. Various configurations can be used for these additional structures and are well known to those skilled in the art. For example, the monitoring devices 210, 310 may be wired to a smartphone, wireless "medallion", and/or MP3-player for powering, signal processing, or audiovisual communication. Moreover, at least some of the electronics illustrated in FIG. 3 may be located in such additional structures, rather than in the monitoring devices 210, 310, themselves.

Figure 12:
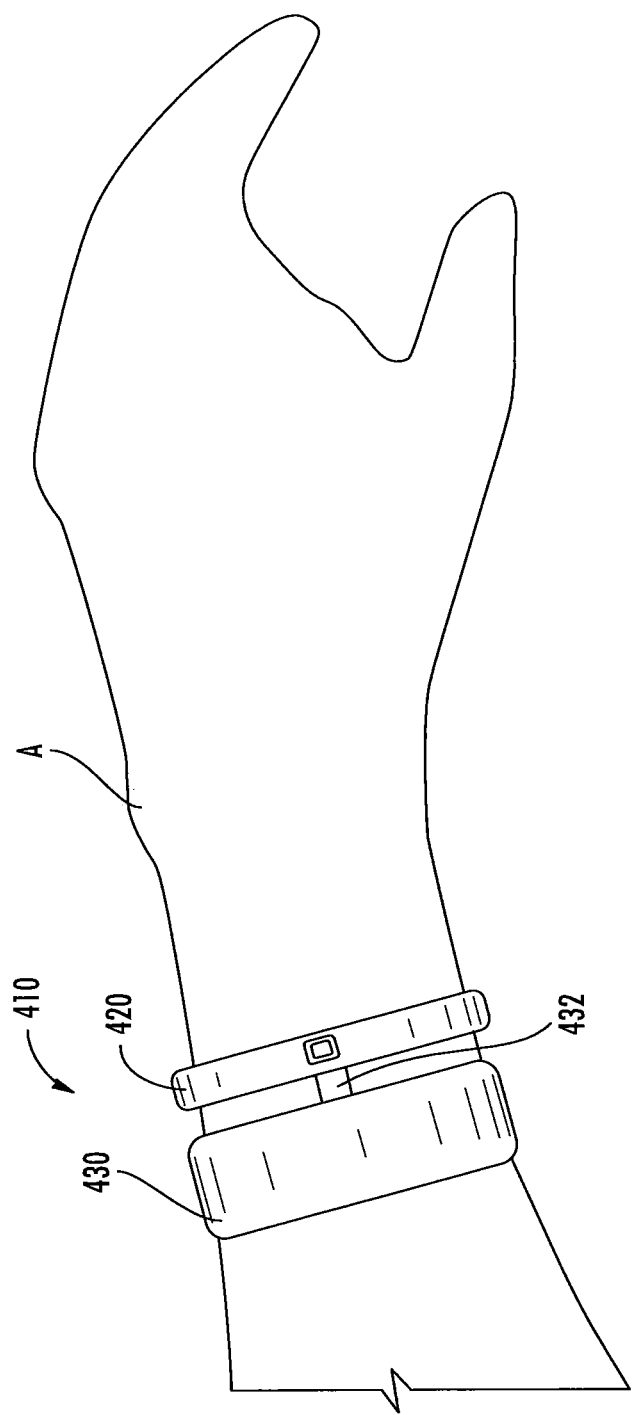
FIG. 12 illustrates a monitoring device configured to be secured to an appendage of a subject, according to some embodiments of the present invention.
Figure 13:
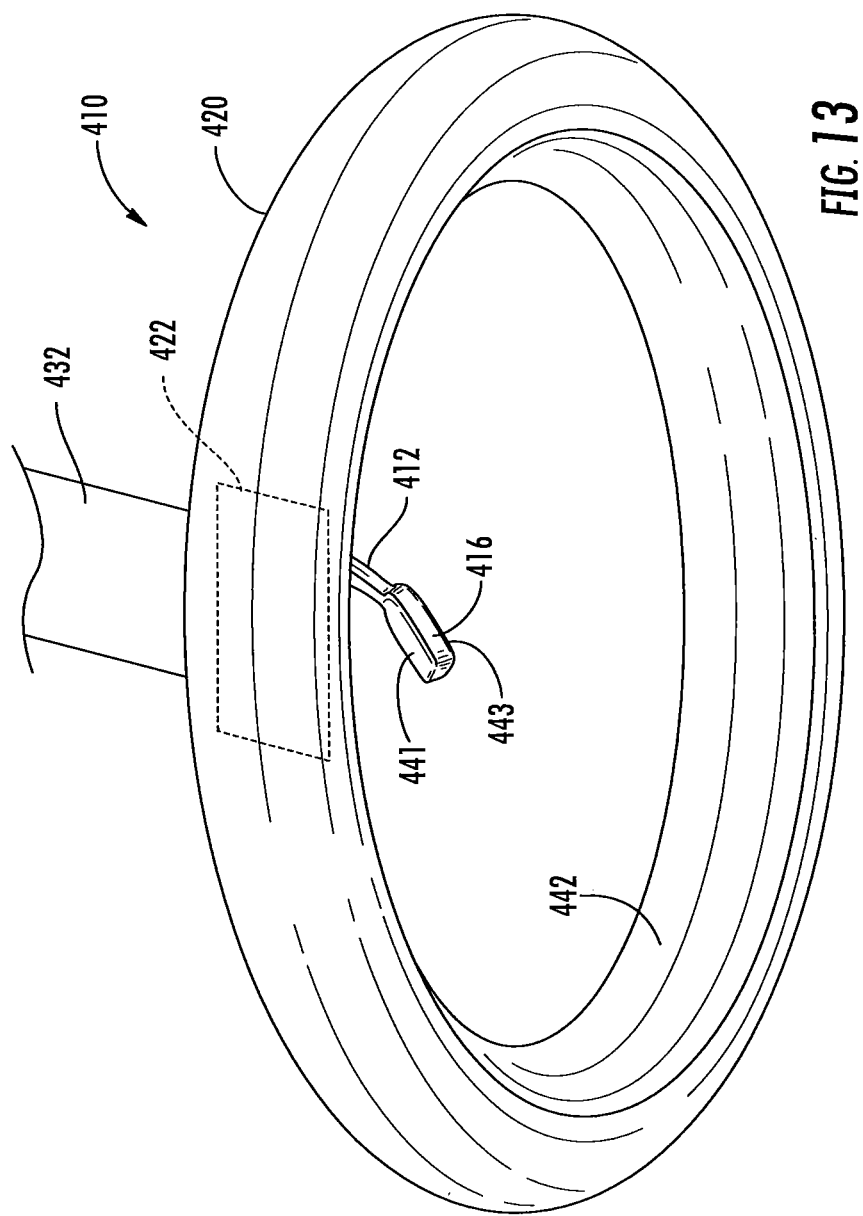
FIG. 13 is a partial perspective view of the monitoring device of FIG. 12 illustrating a sensor band and a sensing element movably secured to the sensor band via a biasing element.

Referring now to FIGS. 12 and 13, a monitoring device 410, according to other embodiments of the present invention, is illustrated. The illustrated monitoring device 410 includes a sensor band 420 configured to be secured to an appendage A (e.g., an arm, wrist, hand, finger, toe, leg, foot, neck, etc.) of a subject, and a sensing element 416 movably secured to the sensor band 420 via a biasing element 412. The biasing element 412 is configured to urge the sensing element 416 into contact with a portion of the appendage A. The biasing element 412 decouples motion of the sensor band 420 from the sensing element 416.

The sensor band 420 has a first mass, and the sensing element 416 has a second mass that is less than the first mass. For example, in some embodiments, the sensor band mass may be at least 10% greater than the sensing element mass, may be at least 20% greater than the sensing element mass, may be at least 30% greater than the sensing element mass, may be at least 40% greater than the sensing element mass, may be at least 50% greater than the sensing element mass, may be at least 60% greater than the sensing element mass, may be at least 70% greater than the sensing element mass, may be at least 80% greater than the sensing element mass, may be at least 90% greater than the sensing element mass, may be at least 100% greater than the sensing element mass, may be 200% or more than the sensing element mass, etc. In general, the mass of the sensor band is preferably larger than that of the sensing element by a sufficient degree so that the sensor band serves as the primary frame of reference (the mechanical support reference) for the monitoring device.

The sensing element 416 may include all of the functionality of the sensing device 16 described above. For example, in summary, the sensing element 416 may include at least one energy emitter 20 (FIG. 3) configured to direct energy at a target region of the appendage A and at least one detector 22 (FIG. 3) configured to detect an energy response signal from the target region or a region adjacent the target region, as described above, to sense physiological signals from the body of the subject. In some embodiments, the biasing element 412 includes a motion sensor (e.g., 24, FIG. 3) configured to detect motion of the biasing element and/or sensing element 416.

In some embodiments, the monitoring device 410 includes a signal processor 26 (FIG. 3) that is configured to receive and process signals produced by the at least one detector 22. The monitoring device 410 may include other components such as one or more analog-to-digital convertors (not shown) for the output of the at least one detector 22, one or more filters such as optical filters (not shown) for removing the effects of time-varying environmental interference, one or more analog and/or digital filters for removing motion artifacts in an energy response signal, passive electronic components, etc., as would be understood by one skilled in the art. The monitoring device 410 may include various other devices, such as other types of physiological sensors and environmental sensors (not shown). The monitoring device 410 may also include at least one wireless module (not shown) for communicating with a remote device, and/or at least one memory storage device (not shown). An exemplary wireless module may include a wireless chip, antenna, or RFID tag. In some embodiments, the wireless module may include a low-range wireless chip or chipset, such as a Bluetooth®, ANT+, and/or ZigBee chip. A battery (not shown), such as a lithium polymer battery or other portable battery, may be included within the monitoring device 410 and may be charged via a USB charge port, for example.

Figure 14:
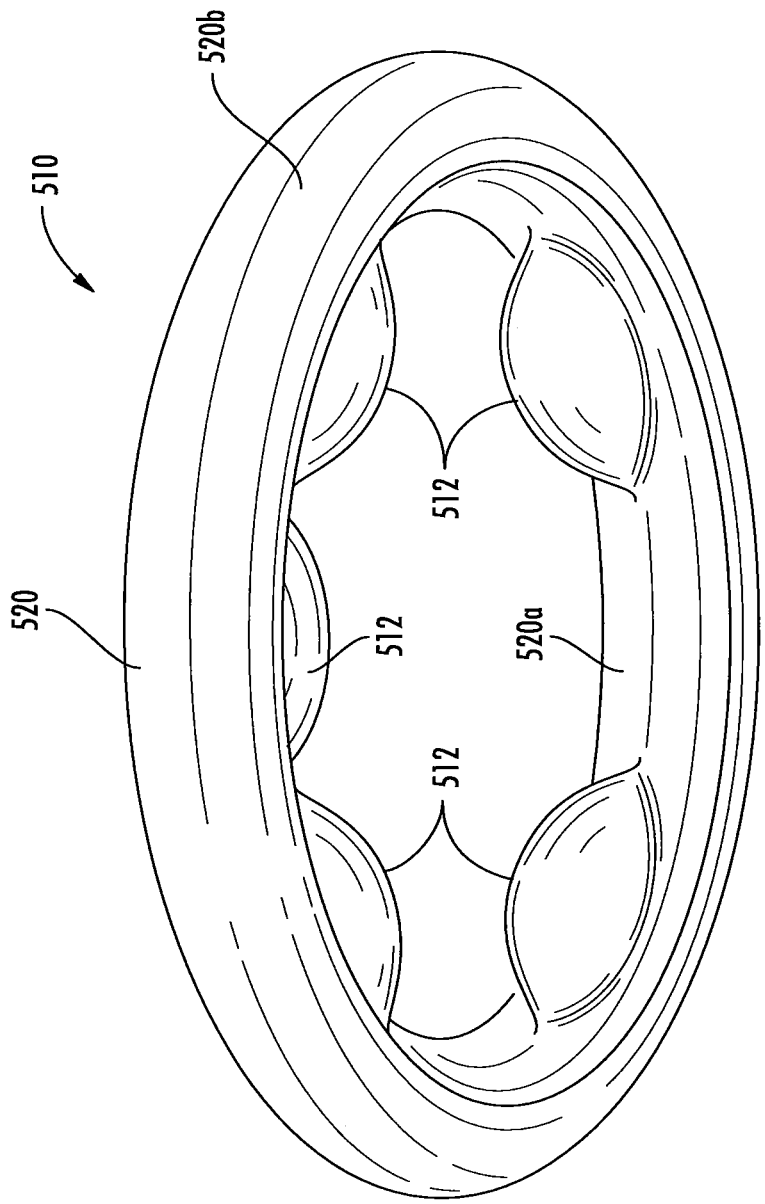
FIG. 14 illustrates a monitoring device configured to be secured to an appendage of a subject, according to some embodiments of the present invention.

In some embodiments, light guides and associated optics, as shown in FIGS. 6 and 7, may be integrated into the sensing element 416 (and 516, FIG. 14). As with the earpiece monitoring device 10 described above, the sensing element 416 may additionally include at least one energy emitter and/or at least one energy detector configured to primarily sense the motion the sensor element 416 itself, such that, utilizing a processor (e.g., 26, FIG. 3), this motion signal can provide a suitable motion noise reference for attenuating motion noise from the physiological signals collected by the sensing element 416.

In some embodiments, the sensor element 416 may include a top portion 441 and an opposite bottom portion 443. An energy emitter and/or detector may be located on the bottom portion 443 to sense physiological information from the appendage of a subject wearing the monitoring device 410, and an energy emitter and/or detector may be located on the top portion 441 to sense motion of the sensor element 416 with respect to the sensor band 420, counterweight 422, and/or inner surface 442 of the sensor band 420. Energy scattered between the top portion 441 of the sensor element 416 and inner surface 442 of the sensor band 420 may coincide with motion between these two surfaces (i.e., sensing element top portion 441 and sensor band inner surface 442), and this information may be used as a noise reference for motion noise attenuation as aforementioned.

In some embodiments, an emitter and/or detector may alternatively be disposed on the inner surface 442 of the sensor band 420, rather than on the top portion 441 of the sensor element 416, or there may be at least one emitter and detector disposed between the inner surface 442 and sensing element top portion 441. In either embodiment, energy is emitted by at least one energy emitter disposed on at least one face (i.e., sensor band inner surface 442, sensing element top portion 441), is modulated in intensity by motion (displacement) between the two portions (i.e., sensor band inner surface 442, sensing element top portion 441), and is detected by an energy detector disposed on at least one of the two portions (i.e., sensor band inner surface 442, sensing element top portion 441). It should be noted that embodiments of the present invention may apply equally well to the earpiece monitoring device 10 of FIG. 2, with respect to the corresponding face of the main body of the monitoring device 10 and the corresponding face of the sensing element 16.

In the illustrated embodiment, the monitoring device 410 may include a second band 430 that is configured to be secured to the appendage A of the subject in adjacent, spaced-apart relationship with the sensor band 420. At least one connecting member or bridge 432 connects the sensor band and second band. In general, the purpose of the bridge 432 is to at least partially decouple motion between the sensor band 420 and second band 430. A plurality of connecting members 432 may be utilized, without limitation. The at least one connecting member 432 may be placed at a distance from the sensing element 416 to increase decoupling of motion of the sensor band 420 from the sensing element 416.

Adding a second band 430 may not be required for overall physiological sensing; however, having a second band 430 may help in further decoupling the sensing element 416 from the motion of other essential electronics surrounding the appendage. For example, the second band 430 may contain a power source (e.g., a battery, etc.) and various heavier electronic components. In such case, the second band 430 may have a mass that is greater than the mass of the sensor band 420 which, in turn, may have a mass greater than that of the sensing element 416. In some embodiments, a counterweight 422 may be embedded within, or otherwise attached to, the sensor band 420 to help keep the sensing element 416 pressed into the appendage A of the subject.

In some embodiments, the counterweight 422 may be located in an area of the sensor band 420 that is opposite that of the sensing element 416. In other embodiments, the counterweight 422 may be a distributed weight that is distributed according to a mathematical function factoring the distance from the sensing element 416. As a particular example, the density of the counterweight 422 may be proportional to the radial distance away from the sensing element 416 such that the peak density is in an area of the sensor band 420 that is opposite that of the sensing element 416. The counterweight 422 can be virtually any material that can be structurally supported by the sensor band 420. In some embodiments, the counterweight 422 may be a greater total mass of plastic used in the housing of the sensor band 420, or a higher density plastic.

In embodiments where one or more light-guides are integrated into the sensing element 416, a light guide may transmit light to the second band 430 through the connecting member 432, such that the emitter and/or detector electronics may also be located on the second band 430. This may further reduce the overall mass of the sensing element 416 and/or sensor band 420.

In some embodiments, one or more motion sensors (e.g., 24, FIG. 3) may be integrated into multiple regions of the overall band 410. For example, one or more motion sensors may be located in the sensor band 420, second band 430, the biasing element 412, and/or the sensor element 416. Each of these regions may have different motion characteristics depending on the type of user motion, and the resulting motion artifacts may corrupt the physiological signal as detected by the detector (e.g., 22, FIG. 3) associated with the sensing element 416. A processor (e.g., 26, FIG. 3) may combine signals (via mixing, averaging, subtracting, applying a transform, and/or the like) from each motion sensor to more effectively characterize the motion noise and thereby facilitates more effective attenuation of motion artifacts from physiological signals detected by a detector of the sensing element 416. Moreover, because the motion signals from each motion sensor may be different during user motion, the processor may additionally be configured to identify the type of user motion by processing the motion signals from multiple motion sensors. As a specific example, there are many examples known to those skilled in the art for utilizing the characteristic multi-axis accelerometer output signals—i.e., the intensities, frequencies, and/or transient responses of multiple accelerometers placed in different locations—measured during a characteristic motion for characterizing different types of movement.

Embodiments of the present invention are not limited to the illustrated arrangement of the sensor band 420 and second band 430. In other embodiments of the present invention, the arrangement of the sensor band 420 and second band 430 relative to each other may be switched from that illustrated in FIG. 12. In some embodiments, the sensor band 420 may be attached to a pair of second bands 430 such that the sensor band is positioned between each second band (e.g., a central sensor band 420 with a second band 430 on each side of the sensor band 420). Various configurations of bands may be utilized in accordance with embodiments of the present invention, as long as the weight of the sensor band 420 and second band 430 are substantially decoupled, such that the bands are not rigidly coupled together.

Figure 15:
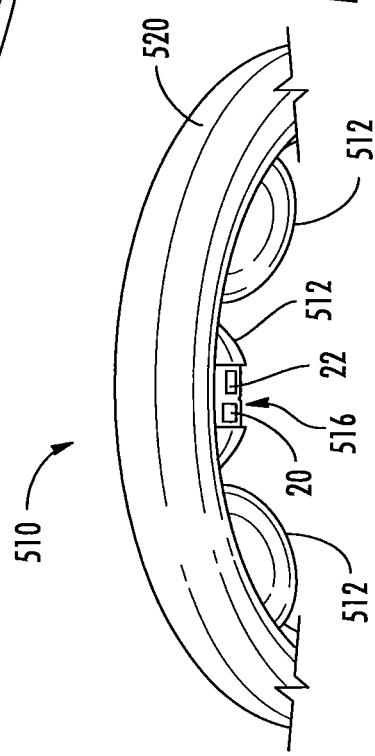
FIG. 15 is a partial view of the monitoring device of FIG. 14 illustrating a sensing element secured to the band inner surface between two of the biasing elements.

Referring to FIGS. 14 and 15, a monitoring device 510, according to other embodiments of the present invention, is illustrated. The illustrated monitoring device 510 includes a band 520 that is configured to be secured to an appendage (e.g., an arm, wrist, finger, toe, leg, neck, etc.) of a subject. The band 520 includes an inner surface 520a and an outer surface 520b. A plurality of biasing elements 512 extend radially outward from the inner surface 520a in spaced-apart relationship and are configured to contact the appendage. A sensing element 516 is secured within one of the biasing elements 512. As illustrated in FIG. 15, the sensing element 516 is recessed within one of the biasing elements such that an energy emitter 20 and a detector 22 are not in contact with the appendage but remain stabilized with respect to the appendage by the biasing elements 512. In another embodiment, the sensing element 516 may extend outwardly from the biasing element 512 such that an energy emitter 20 and a detector 22 are in contact with the appendage and remain stabilized with respect to the appendage.

The biasing elements 512 may be formed from silicone, polymeric material, rubber, soft plastic, other elastomeric materials, or other compressible materials that can act as cushions. In some cases, the biasing elements 512 may be fluid filled solid elements or may be heterogeneous elements composed of one or more compressible materials, layers, and/or over-molded parts. Various shapes, configurations, and materials may be utilized to implement the biasing elements 512, without limitation. The biasing elements 512 help keep the sensing element 516 in place in proximity to (or against) an appendage. The biasing elements 512 may have a durometer range from about 10 (Type OO—ASTM D2240) to 80 (Type A—ASTM D2240), and a hardness range of about 20-50 Shore A. Exemplary resilient material that may be used as a biasing element 512 includes, but is not limited to, silicone (Dow Corning Corp., Midland, Mich.). However, various other materials may be used.

The sensing element 516 may include all of the functionality of the sensing device 16 described above. For example, the sensing element 516 may include at least one energy emitter 20 (FIG. 3) configured to direct energy at a target region of the appendage and at least one detector 22 (FIG. 3) configured to detect an energy response signal from the target region and/or a region adjacent the target region, as described above. In some embodiments, one or more of the biasing elements 512 includes a motion sensor (not shown) configured to detect motion of the biasing element 512 and/or sensing element 516.

In some embodiments, the monitoring device 510 includes a signal processor 26 (FIG. 3) that is configured to receive and process signals produced by the at least one detector 22. The monitoring device 510 may include other components such as one or more analog-to-digital convertors (not shown) for the output of the at least one detector 22, one or more filters such as optical filters (not shown) for removing the effects of time-varying environmental interference, one or more analog and/or digital filters for removing motion artifacts in an energy response signal, passive electronic components, etc., as would be understood by one skilled in the art. The monitoring device 510 may include various other devices, such as other types of physiological sensors and environmental sensors (not shown). The monitoring device 510 may also include at least one wireless module (not shown) for communicating with a remote device, and/or at least one memory storage device (not shown). An exemplary wireless module may include a wireless chip, antenna, or RFID tag. In some embodiments, the wireless module may include a low-range wireless chip or chipset, such as a Bluetooth®, ANT+, and/or ZigBee chip. A battery (not shown), such as a lithium polymer battery or other portable battery, may be included within the monitoring device 510 and may be charged via a USB charge port, for example.

Alternating shapes of the biasing elements 512 may be useful for providing additional mechanical support as different shapes touching the skin may product stabilizing forces in different vectors (directions and/or magnitudes) across the skin which collectively may provide an overall better support of the band 520 against an appendage.

Figure 16:
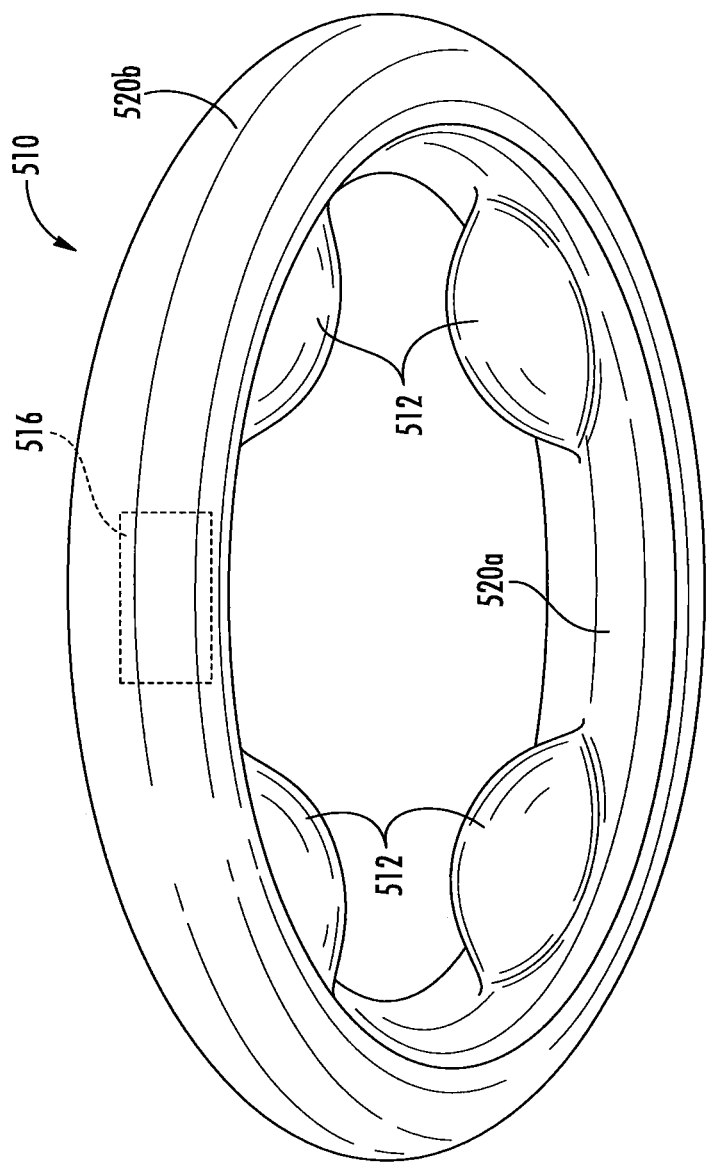
FIG. 16 illustrates a monitoring device configured to be secured to an appendage of a subject, according to some embodiments of the present invention.
Figure 16A:
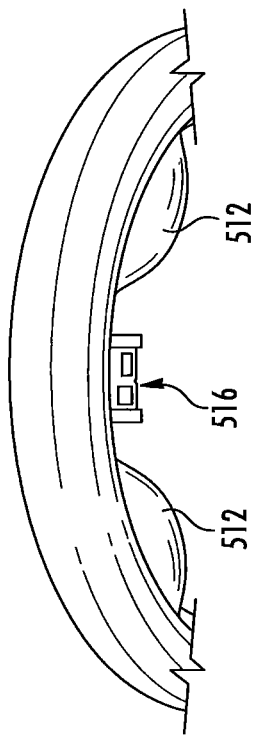
FIG. 16A is a partial view of the monitoring device of FIG. 16 illustrating a sensing element secured to the band inner surface between two of the biasing elements.

Referring to FIGS. 16 and 16A, a monitoring device 510, according to other embodiments of the present invention, is illustrated. The illustrated monitoring device 510 includes a band 520 that is configured to be secured to an appendage (e.g., an arm, wrist, finger, toe, leg, neck, hand, foot, etc.) of a subject. The band 520 includes an inner surface 520*a* and an outer surface 520*b*. A plurality of biasing elements 512 extend radially outward from the inner surface 520*a* in spaced-apart relationship and are configured to contact the appendage. A sensing element 516 is secured to the band inner surface 520*a* between adjacent biasing elements 512. In some embodiments, the sensing element 516 extends outwardly from the band inner surface 520*a* such that an energy emitter 20 and a detector 22 are not in contact with the appendage but remain stabilized with respect to the appendage by the biasing elements. In other embodiments, the sensing element 516 extends outwardly from the band inner surface 520*a* such that an energy emitter 20 and a detector 22 are in contact with the appendage and remain stabilized with respect to the appendage.

Alternating shapes of the biasing elements 512 may be useful for providing additional mechanical support as different shapes touching the skin may product stabilizing forces in different vectors (directions and/or magnitudes) across the skin which collectively may provide an overall better support of the band 520 against an appendage.

Figure 17:
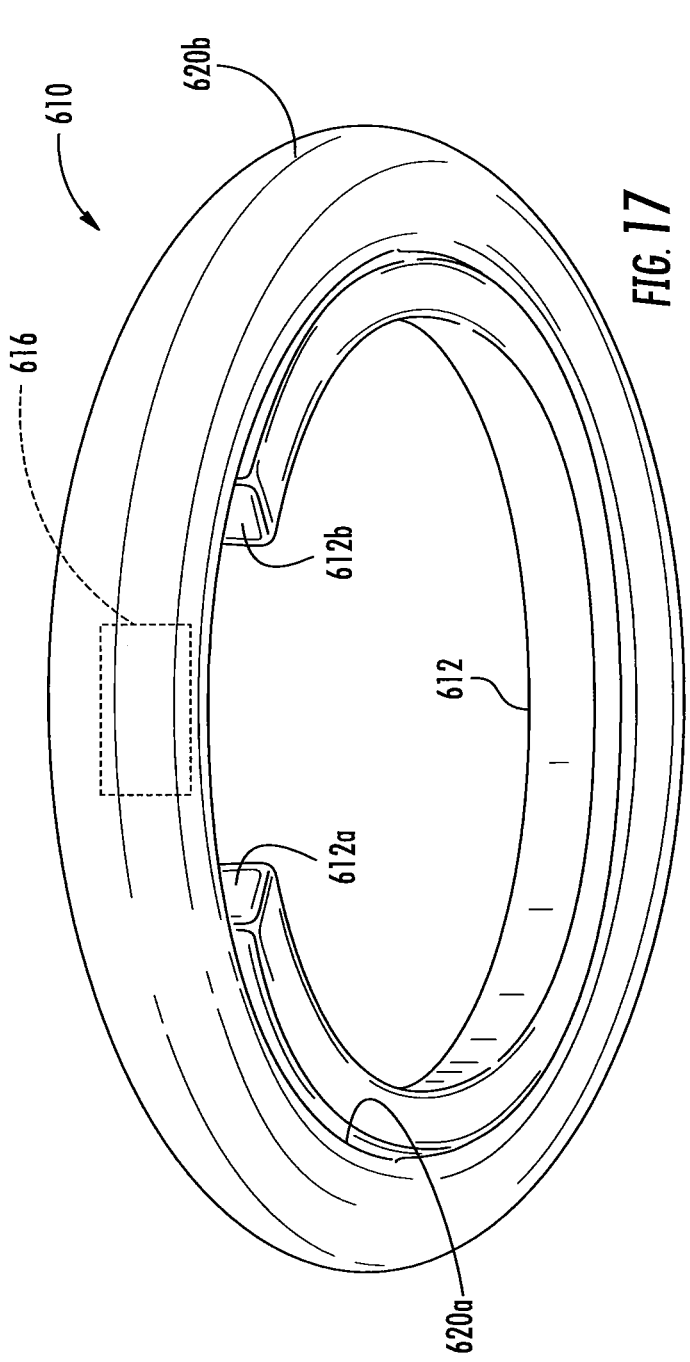
FIG. 17 illustrates a monitoring device configured to be secured to an appendage of a subject, according to some embodiments of the present invention.
Figure 17B:
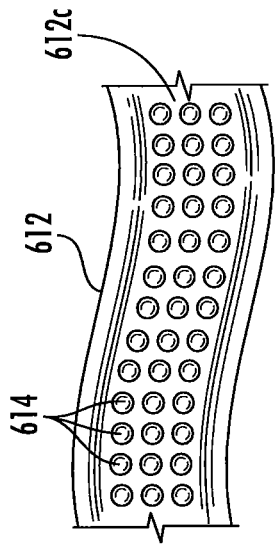
FIG. 17B is a partial view of the resilient support of the monitoring device of FIG. 17 illustrating a textured surface thereof, according to some embodiments of the present invention.
Figure 17A:
FIG. 17A is a partial view of the monitoring device of FIG. 17 illustrating a sensing element secured to the band inner surface.

Referring to FIGS. 17, 17A and 17B, a monitoring device 610, according to other embodiments of the present invention, is illustrated. The illustrated monitoring device 610 includes a band 620 that is configured to be secured to an appendage (e.g., an arm, wrist, finger, toe, leg, neck, hand, foot, etc.) of a subject. The band 620 includes an inner surface 620*a* and an outer surface 620*b*. A single, elongated biasing element 612 is located on the inside of the band 620 near the inner surface 620*a*. The biasing element 612 is configured to compress and conform to the appendage of a subject when the band is worn on the appendage. The biasing element 612 has opposite ends 612*a*, 612*b* and the biasing element 612 extends circumferentially around the band inner surface 620*a* such that the biasing element ends are in adjacent, spaced-apart relationship.

A sensing element 616 is secured to the band inner surface 620*a* between the spaced-apart end portions 612*a*, 612*b* of the biasing element 612. In some embodiments, the sensing element 616 extends outwardly from the band inner surface 620*a* such that an energy emitter 20 and a detector 22 are not in contact with the appendage but remain stabilized with respect to the appendage by the biasing element 612. In other embodiments, the sensing element 616 extends outwardly from the band inner surface 620*a* such that an energy emitter 20 and a detector 22 are in contact with the appendage and remain stabilized with respect to the appendage. The sensing element 616 may include all of the functionality of the sensing device 16 described above. For example, the sensing element 616 may include at least one energy emitter 20 (FIG. 3) configured to direct energy at a target region of the ear and at least one detector 22 (FIG. 3) configured to detect an energy response signal from the target region or a region adjacent the target region, as described above.

In some embodiments, the monitoring device 610 includes a signal processor 26 (FIG. 3) that is configured to receive and process signals produced by the at least one detector 22. The monitoring device 610 may include other components such as one or more analog-to-digital convertors (not shown) for the output of the at least one detector 22, one or more filters such as optical filters (not shown) for removing the effects of time-varying environmental interference, one or more analog and/or digital filters for removing motion artifacts in an energy response signal, passive electronic components, etc., as would be understood by one skilled in the art. The monitoring device 610 may include various other devices, such as other types of physiological sensors and environmental sensors (not shown). The monitoring device 610 may also include at least one wireless module (not shown) for communicating with a remote device, and/or at least one memory storage device (not shown). An exemplary wireless module may include a wireless chip, antenna, or RFID tag. In some embodiments, the wireless module may include a low-range wireless chip or chipset, such as a Bluetooth®, ANT+, and/or ZigBee chip. A battery (not shown), such as a lithium polymer battery or other portable battery, may be included within the monitoring device 610 and may be charged via a USB charge port, for example.

One or more portions (including all) of the biasing element surface 612*a* that engages the skin have a textured configuration. In the illustrated embodiment of FIG. 17B, the portion of the surface 612*a* with a textured configuration includes a plurality of raised portions or protrusions 614. These protrusions 614 facilitate breathability of the band 620 when touching the skin. The textured surface portions may have virtually any shape to support spring compression and breathability, but spherical protrusions or flat protrusions may be best for manufacturing simplicity and comfort. In some embodiments the protrusions 614 may have a height, spacing, and diameter in the range of between about 0.1 mm and about 5.0 mm. For example, a protrusion 614 may have a height of between about 0.1 mm and about 5.0 mm, a diameter of between about 0.1 mm and about 5.0 mm, and adjacent protrusions 614 may be spaced apart between about 0.1 mm and about 5.0 mm. However, various other ranges are possible.

In some embodiments, alternating shapes of textured portions may be useful for providing additional mechanical support as different shapes touching the skin may product stabilizing forces in different vectors (directions and/or magnitudes) across the skin which collectively may provide an overall better support of the band 620 against the appendage The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. As an example, although many drawings in this invention have shown sensing elements located within the inner region of the ear, the invention could be applied to designs where the sensing element is configured to be placed on the outside of the ear, such as a location behind the earlobe or in front of the tragus. Accordingly, all such modifications are intended to be included within the scope of this invention as defined in the claims. The invention is defined by the following claims, with equivalents of the claims to be included therein.

That which is claimed is:

1. A monitoring device, comprising:
   a sensor band configured to be secured around a wrist of a subject, wherein the sensor band has a first mass;
   a sensing element secured to the sensor band, wherein the sensing element has a second mass that is less than the first mass;
   a second band configured to be secured around the wrist of the subject in adjacent, spaced-apart relationship with the sensor band, wherein the second band has a third mass that is greater than the first mass; and
   at least one member connecting the sensor band and the second band.

2. The monitoring device of claim 1, wherein the sensing element is movably secured to the sensor band via a biasing element, wherein the biasing element is configured to urge the sensing element into contact with a portion of the wrist, wherein the biasing element at least partially decouples motion of the sensor band from the sensing element, and wherein the at least one member at least partially decouples motion between the sensor band and the second band.

3. The monitoring device of claim 2, wherein the biasing element comprises a motion sensor configured to detect motion of the biasing element and/or sensing element.

4. The monitoring device of claim 1, wherein the sensor band comprises at least one counterweight.

5. The monitoring device of claim 1, wherein the sensing element comprises at least one energy emitter configured to direct energy at a target region of the wrist and at least one detector configured to detect an energy response signal containing physiological information from the target region or a region adjacent to the target region.

6. The monitoring device of claim 5, further comprising at least one filter configured to at least partially remove motion artifacts from the energy response signal.

7. The monitoring device of claim 5, further comprising at least one wireless module configured to communicate with a remote device.

8. The monitoring device of claim 5, further comprising a signal processor configured to receive and process signals produced by the at least one detector.

9. The monitoring device of claim 8, wherein the sensor band comprises a plurality of motion sensors, and wherein the signal processor is configured to combine signals from the motion sensors and attenuate motion artifacts from the signals produced by the at least one detector.

10. The monitoring device of claim 5, wherein the at least one energy emitter is configured to direct electromagnetic radiation, mechanical energy, acoustical energy, electrical energy, and/or thermal energy at the target region, and wherein the at least one detector is configured to detect electromagnetic radiation, mechanical energy, acoustical energy, electrical energy, and/or thermal energy.

11. The monitoring device of claim 5, wherein the at least one energy emitter comprises at least one optical emitter and wherein the at least one detector comprises at least one optical detector.

12. The monitoring device of claim 11, further comprising at least one filter configured to remove time-varying environmental interference from signals produced by the at least one optical detector.

13. The monitoring device of claim 11, wherein the sensing element comprises at least one light guide in optical communication with the at least one optical emitter and/or the at least one optical detector, wherein the at least one light guide delivers light from the at least one optical emitter to the target region and/or delivers an optical energy response signal containing physiological information from the target region or a region adjacent to the target region to the at least one optical detector.

14. The monitoring device of claim 5, wherein the sensing element comprises a surface having at least one window through which energy passes from the at least one energy emitter, and through which energy is collected by the at least one detector.

15. The monitoring device of claim 1, wherein the first mass is at least about 1.25 times greater than the second mass.

16. The monitoring device of claim 1, wherein the sensing element comprises first and second portions, and further comprising at least one energy emitter and at least one detector located at the first portion to sense physiological information from the wrist of the subject, and wherein the sensor band comprises an additional energy emitter and detector configured to sense motion of the sensing element second portion with respect to the sensor band.

17. The monitoring device of claim 1, wherein the second band comprises at least one optical emitter and at least one optical detector, and further comprising at least one light guide integrated into the sensing element that is in optical communication with the at least one optical emitter and the at least one optical detector via the at least one member connecting the sensor band and the second band, wherein the at least one light guide delivers light to the target region from the at least one optical emitter and delivers an optical energy response signal containing physiological information from the target region or a region adjacent to the target region to the at least one optical detector.

18. A monitoring device, comprising:
a sensor band configured to be secured around an appendage of a subject, wherein the appendage is one of an arm, wrist, hand, finger, toe, leg, foot, neck, and wherein the sensor band has a first mass;
a sensing element secured to the sensor band, wherein the sensing element has a second mass that is less than the first mass, wherein the sensing element comprises first and second portions, and further comprising at least one energy emitter and at least one detector located at the first portion to sense physiological information from the appendage of the subject, and further comprising an additional energy emitter and detector located at the second portion to sense motion of the sensing element with respect to the sensor band;
a second band configured to be secured to the appendage of the subject in adjacent, spaced-apart relationship with the sensor band; and
at least one member connecting the sensor band and the second band.

19. A monitoring device, comprising:
a sensor band configured to be secured around a wrist of a subject, wherein the sensor band has a first mass;
a sensing element secured to the sensor band, wherein the sensing element has a second mass that is less than the first mass, wherein the sensing element comprises at least one optical emitter configured to direct optical energy at a target region of the wrist and at least one optical detector configured to detect an optical energy response signal containing physiological information from the target region or a region adjacent to the target region;
a second band configured to be secured around the wrist of the subject in adjacent, spaced-apart relationship with the sensor band; and
at least one member connecting the sensor band and the second band.

20. The monitoring device of claim 19, wherein the sensing element is movably secured to the sensor band via a biasing element, wherein the biasing element is configured to urge the sensing element into contact with a portion of the wrist, wherein the biasing element at least partially decouples motion of the sensor band from the sensing element, and wherein the at least one member at least partially decouples motion between the sensor band and the second band.

21. The monitoring device of claim 20, wherein the biasing element comprises a motion sensor configured to detect motion of the biasing element and/or sensing element.

22. The monitoring device of claim 19, wherein the second band has a third mass that is greater than the first mass.

23. The monitoring device of claim 19, wherein the sensor band comprises at least one counterweight.

24. The monitoring device of claim 19, further comprising at least one filter configured to at least partially remove motion artifacts from the optical energy response signal.

25. The monitoring device of claim 19, further comprising at least one wireless module configured to communicate with a remote device.

26. The monitoring device of claim 19, further comprising a signal processor configured to receive and process signals produced by the at least one optical detector.

27. The monitoring device of claim 26, wherein the sensor band comprises a plurality of motion sensors, and wherein the signal processor is configured to combine signals from the motion sensors and attenuate motion artifacts from the signals produced by the at least one optical detector.

28. The monitoring device of claim 19, further comprising at least one filter configured to remove time-varying environmental interference from signals produced by the at least one optical detector.

29. The monitoring device of claim 19, wherein the sensing element comprises at least one light guide in optical communication with the at least one optical emitter and/or the at least one optical detector, wherein the at least one light guide delivers light from the at least one optical emitter to the target region and/or delivers an optical energy response signal containing physiological information from the target region or a region adjacent to the target region to the at least one optical detector.

30. The monitoring device of claim 19, wherein the sensing element comprises a surface having at least one window through which optical energy passes from the at least one optical emitter, and through which optical energy is collected by the at least one optical detector.

31. The monitoring device of claim 19, wherein the first mass is at least about 1.25 times greater than the second mass.

32. The monitoring device of claim 19, wherein the sensing element comprises first and second portions, and wherein the at least one optical emitter and the at least one optical detector are located at the first portion to direct optical energy at the target region of the wrist and to detect the optical energy response signal containing physiological information from the target region or a region adjacent to the target region, and further comprising an energy emitter and detector located at the second portion to sense motion of the sensing element with respect to the sensor band.

33. The monitoring device of claim 19, wherein the sensing element comprises first and second portions, and wherein the at least one optical emitter and the at least one optical detector are located at the first portion to direct optical energy at the target region of the wrist and to detect the optical energy response signal containing physiological information from the target region or a region adjacent to the target region, and wherein the sensor band comprises an energy emitter and detector configured to sense motion of the sensing element second portion with respect to the sensor band.

* * * * *